(12) United States Patent
Zhang et al.

(10) Patent No.: US 7,141,407 B2
(45) Date of Patent: Nov. 28, 2006

(54) CHICKWEED BIOHERBICIDES

(75) Inventors: Wenming Zhang, Ottawa (CA); Michelle Sulz, Andrew (CA)

(73) Assignee: Alberta Research Council Inc., Edmonton (CA)

( * ) Notice: Subject to any disclaimer, the term of this patent is extended or adjusted under 35 U.S.C. 154(b) by 41 days.

(21) Appl. No.: 10/793,643

(22) Filed: Mar. 5, 2004

(65) Prior Publication Data

US 2004/0254075 A1 Dec. 16, 2004

(30) Foreign Application Priority Data

Mar. 7, 2003 (CA) .................................. 2421373

(51) Int. Cl.
*C12N 1/20* (2006.01)
*A01N 63/00* (2006.01)
(52) U.S. Cl. .............................. 435/252.1; 435/253.3; 435/822; 435/874; 500/117; 424/93.47
(58) Field of Classification Search ............. 435/252.1, 435/252.3, 822, 874; 504/117; 424/93.47
See application file for complete search history.

(56) References Cited

OTHER PUBLICATIONS

Allen, R.N., et. al., "Bacterial Blight of *Vicia sativa*: Aetiology of Disease and Indentification of the Pathogen," *Aust. J. Biol. Sci.* 23:597-606, Commonwealth Scientific And Industrial Research Organization (1970).
Bagsic-Opulencia, R.D., et. al., "Use of ribotyping and random amplified polymorphic DNA to differentiate isolates of *Burkholderia andropogonis*,"*J. Appl. Microbiol.* 91:686-696, The Society for Applied Microbiology (2001).
Bateman, G., "Caryophyllidae," in *Flowering Plants of the World*, Bateman, G., ed., Croom Helm Publishers Ltd., Beckenham, Kent, UK, pp. 63-76 (1985).
Boyette, C.D., et. al., "Progress in the Production, Formulation, and Application of Mycoherbicides," in *Microbial Control of Weeds*, TeBeest, D.O., ed., Chapman & Hill, New York, NY, pp. 209-222 (1991).
Burkholder, W.H., "A Bacterial Disease of Clover and Velvet Beans," *Phytopathology* 47:48-50, American Phytopathological Society (1957).
Caruso, F.L., "Bacterial Blight of Chickpea Incited by *Pseudomonas adnropogonis,"Plant Disease* 68:910-913, American Phytopathological Society (1984).
Charudattan, R., "Biological control of weeds by means of plant pathogens: Significance for Integrated weed management in modem agro-ecology," *BioControl* 46:229-260, Kluwer Academic Publishers (2001).
Churchill, B.W., "Mass Production of Microorganisms for Biological Control," in *Biological Control of Weeds with Plant Pathogens*, Chardattan, R., and Walker, H.L., eds., John Wiley & Sons, New York, NY, pp. 139-156 (1982).
Coenye, T., et al., "Genotypic and chemotaxonomic evidence for the reclassification of *Pseudomonas woodsii* (Smith 1911) Stevens 1925 as *Burkholderia andropogonis* (Smith 1911) Gillis et al. 1995," *Int. J. Syst. Evol. Microbiol.* 51:183-185, Society for General Microbiology (2001).
Coenye, T., et. al., "*Burkholderia cocovenenans* (van Damme et al. 1960) Gillis et al. 1995 and *Burkholderia vandii* Urakami et al. 1994 are junior synonyms of *Burkholderia gladioli* (Severini 1913) Yabuuchi et al., 1993 and *Burkholderia plantaril* (Azegaml et al. 1987) Urakaml et al. 1994, respectively," *Int. J. Syst. Bacteriology* 49:37-42, Society for General Microbiology (1999).
Coenye, T., et. al., "*Burkholderia fungorum* sp. nov. and *Burkholderia caledonica* sp. nov., two new species isolated from the environment, animals and human clinical samples," *Int. J. Syst. Evol. Microbiol.* 51:1099-1107, Society for General Microbiology (2001).
Coenye, T., et. al., "*Burkholderia ambifaria* sp. nov., a novel member of the *Burkholderia cepacia* complex including biocontrol and cystic fibrosis-related isolates," *Int. J. Syst. Evol. Microbiol.* 51:1481-1490, Society for General Microbiology (2001).
Cronquist, A., "III. Subclass CARYOPHYLLIDAE Takhtajan 1966," in *An Integrated System of Classification of Flowering Plants*, Columbia University Press, New York, NY, pp. 231-276 (1981).
Devine, M.D., et. al., "Inhibition of Acetolactate synthase in Susceptible and Resistant Biotypes of *Stellaria media," Pestic. Sci.* 31:273-280, Wiley and Sons (1991).
Duke, S.O., et. al., "Chemicals from nature for weed management," *Weed Science 50*:138-151, Weed Science Society of America (Apr. 2002).
Gillis, M., et. al., "Polyphasic Taxonomy in the Genus *Burkholderia* Leading to an Emended Description of the Genus and Proposition of *Burkholderia vietnamiensis* sp. nov. for $N_2$-Fixing Isolates from Rice in Vietnam," *Int. J. Syst. Bacteriol.* 45:274-289, International Union of Microbiological Societies (1995).
Gomez, K.A., and Gomez, A.A., "7.2 Data That Violate Some Assumptions of the Analysis of Variance," in *Statistical Procedures for Agricultural Research*, Second Edition, John Wiley & Sons, Inc., New York, NY, pp. 294-308 (1984).
Gomez, K.A., and Gomez, A.A., "Test for Homogeneity of Variance," in *Statistical Procedures for Agricultural Research*, Second edition, John Wiley & Sons, Inc., New York, NY, pp. 469-477 (1984).
Goto, M., and Starr, M.P., "A comparative study of *Pseudomonas andropogonis, P. stizolobii* and *P. alboprecipitans," Ann. Phytopath. Soc. Japan* 37:233-241, Nihon Shokubusu Byori Gakkai (1971).

(Continued)

*Primary Examiner*—Vera Afremova
(74) *Attorney, Agent, or Firm*—Sterne, Kessler, Goldstein & Fox P.L.L.C.

(57) ABSTRACT

The present invention relates to the use of a strain of *Burkholderia andropogonis* for controlling the growth of a weed belonging to the order Caryophyllales. The present invention also provides a method for suppressing weed growth, comprising applying a strain of *Burkholderia andropogonis* to a weed belonging to the order Caryophyllales. Also provided is a biocontrol composition for controlling the growth of a weed belonging to the order Caryophyllales, the composition comprising a strain of *Burkholderia andropogonis*, and a suitable medium.

17 Claims, 18 Drawing Sheets

OTHER PUBLICATIONS

Hall, L.M., and Devine, M.D., "Cross-Resistance of a Chlorosulfuron-Resistant Biotype of *Stellaria media* to a Triazolophyridmidine Herbicide," *Plant Physiol.* 93:962-966, and, a corrections page. American Society of Plant Physiologists (1990).

Hayward, A.C., "A Bacterial Disease of Clover in Hawaii," *Plant Disease Reporter* 56:446-450, Hawaii Agricultural Experiment Station (1972).

Holm, L.G., et. al., "*Stellaria media* (L.) Cyrill. Caryophyllaceae, Pink Family," in *The World's Worst Weeds: Distribution and Biology*, The University Press of Hawaii, Honolulu, HI, pp. 450-455 (1977).

Holm, L.G., et. al., "White or Irish Potatoes, *Solanum tuberosum* L. Solanaceae, Nightshade Famity," in *The World's Worst Weeds: Distribution and Biology*, The University Press of Hawaii, Honolulu, HI, pp. 509-511 (1977).

Holm, L.G., et. al., "Sugar Beets, *Beta vulgaris* L. var. *altissima* Rossig. Chenopodiaceae, Goosefoot Family," in *The World's Worst Weeds: Distribution and Biology*, The University Press of Hawaii, Honolulu, HI, p. 530 (1977).

Holm, L.G., et. al., "Figure 216. Weeds of sugar beets and the main production areas across the world," in *The World's Worst Weeds: Distribution and Biology*, The University Press of Hawaii, Honolulu, HI, p. 531 (1977).

Holm, L.G., et. al., "Wheat, *Triticum aestivum* L. em. Thell. And *Triticum durum* Desf. Poaceae (also Gramineae), Grass Family," in *The World's Worst Weeds: Distribution and Biology*, The University Press of Hawaii, Honolulu, HI, pp. 541-542 (1977).

Horsfall, J.G., and Barrett, R.W., "An improved grading system for measuring plant diseases," *Phytopathol.* 35:655, The American Phytopathological Society (1945).

Hu, F.-P., et. al., "Numerical Analysis and Determinative Tests for Nonfluorescent Plant Pathogenic *Pseudomonas* spp. and Genomic Analysis and Reclassification of Species Related to *Psudomonas avanae* Manns 1909," *Int. J. Syst. Bacteriol.* 41:516-525, International Union of Microbiological Societies (1991).

Hutchinson, J., "Tribe 40. Vicieae," in *The Genera of Glowering Plants*, Oxford at the Clarendon Press, Oxford, UK, pp. 452-454 (1964).

Jackson, M.A., "Optimizing nutritional conditions for the liquid culture production of effective fungal biological control agents," *J. Ind. Microbiol. Biotech.* 19:180-187, Society for Industrial Microbiology (1997).

Jalas, J., and Suominen, J., "6. Carophyllaceae (Alsinoideae and Paronychioideae)," in *Atlas Florae Europaeae: Distribution of vascular plants in Europe III*, Cambridge University Press, Cambridge, UK, pp. 11, 72, 74, 75, 104-107, 113, 133-135, 158, 160 (1987).

Jalas, J., and Suominen, J., "7. Carophyllaceae (Silenoideae)," in *Atlas Florae uropaeae: Distribution of vascular plants in Europe III*, Cambridge University Press, Cambridge, UK, pp. 55-57, 59, 61, 90, 91, 124, 128, 140, 163-165 (1987).

Joohnson, D.R., et. al., "Controlling Weeds with Phytopathogenic Bacteria," *Weed Technology* 10:621-624, Weed Science Society of America (1996).

Lane, D.J., "16S/23S rRNA Sequencing," in *Nucleic Acid Techniques in Bacterial Systematics*, Stackebrandt, E., and Goodfellow, M., eds., John Wiley and Sons, New York, NY, pp. 115-147 (1991).

Liu, D.L.-Y., and Christians, N.E., "Isolation and Identification of Root-Inhibiting Compounds from Corn Gluten Hydrolysate," *Journal of Plant Growth Regulation* 13:227-230, Springer-Verlag (1994)Lane, D.J., "16S/23S rRNA Sequencing," in *Nucleic Acid Techniques in Bacterial Systematics*, Stackebrandt, E., and Goodfellow, M., eds., John Wiley and Sons, New York, NY, pp. 115-147 (1991).

Lutman, P.J.W., and Heath, C.R., "Variations in the resistance of *Stellaria media* to mecoprop due to biotype, application method and 1-aminobenzotriazole," *Weed Research* 30:129-137, Blackwell Scientific Publications (1990).

Mann, H.H., and Barnes, T.W., "The competition between barley and certain weeds under controlled conditions: IV. Competition with *Stellaria media*," *Ann. Appl. Biol.* 37:139-148, Biochemical Society (1950).

Martens, J.W., et. al., "Index," in *Diseases of Field Crops in Canada: an Illustrated Compendium*, The Canadian Phytopathological Society, Ottawa, Ont., pp. 156-160 (1994).

Mitchell, R.E., and Frey, E.J., "Rhizobitoxine and hydroxythreonine production by *Pseudomones andropogonis* strains, and the implications to plant disease," *Physiol. And Mol. Plant Pathol.* 32 : 335-341, Academic Press, Ltd. (1988).

O'Donovan, J.R., et. al., "Investigation of a chlorosulfuron-resistant chickweed [*Stellaria medie* (L.) Will.] population," *Can. J. Plant. Sci.* 74:693-697, Agricultural Institute of Canada (1994).

Palleroni, N.J., "Family I. *Pseudomonadaceae* Winslow, Broadhurst, Buchanan Krumwiede, Rogers and Smith 1917, 555," in *Bergey's Manual of Systematic Bacteriology*, Krieg, N.R., and Holt, J.G., eds., Williams and Wilkins, Baltimore, MD, pp. 141-199 (1984).

SAS Institute, Inc., "Chapter 11: The ANOVA Procedure," in *SAS/STAT™ Guide for Personal Computers, Version 6 Edition*, SAS Institute, Inc., Cary, NC, pp. 125-154 (1987).

Moffett, M.L., et. al., "Five new hosts of *Pseudomonas andropogonis* occurring in eastern Australia: host range and characterization of isolates," *Plant Pathology* 35:34-43, Blackwell Scientific Publications (1986).

Moss, E.H., "CARYOPHYLLACEAE/Pink Family," in *Flora of Alberta: A manual of flowering plants, Conifers, Ferns and Fern Allies found growing without Cultivation in the Province of Alberta, Canada*, University of Toronto Press, pp. 253-260 (1983).

Nishiyama, K., et al., "Bacterial black rot of tulip caused by *Pseudomonas andropogonis*," *Ann. Phytopath. Soc. Japan* 45:668-674, Nihon Shokubutsu Byori Gakkai (1979).

Scoggan, H.J., "Caryophyllaceae," in *The Flora of Canada: Part 3—Dicotylendoneae* (*Saururaceae to Violaceae*, National Museums of Canada, Ottawa, Canada, pp. 673-710 (1978).

Stead, D.E., "Grouping of Plant-Pathogenic and Some Other *Pseudomonas* spp. by Using Cellular Fatty Acid Profiles," *Int. J. Syst. Bacteriol.* 42:281-295, Society for General Microbiology (1992).

Stowell, L.J., et. al., "Fermentation alternatives for commercial production of a mycoherbicide," in *Novel Microbial Products for Medicine and Agriculture*, Demain, A.L., et. al., eds., Society for Industrial Microbiology, pp. 219-227 (1989).

Templeton, G.E., "Biological Herbicides: Discovery, Development, Deployment," *Weed Science* 30:430-433, Weed Science Society Of America (1982).

Thomas, A.G., "Weed population shifts in Alberta," *proceedings*, p. 88, 1997 ECW Meetings, Charlottetown, PEI, Abstract No. PO-07.

Thomas, A.G., et. al., "Changes in weed distributions indicated by quantitative surveys in the prairie provinces of Canada over 10 years," *Proceedings of the 3th Annual WSSA Conference* 38:74, Library of Social Science, Abstract No. 15.9.4 (1998).

Toms, H.N.W., "Plant Diseases of Southern British Columbia—A host index," *Canadian Plant Disease Survey* 44:143-225, Res. Br. Can. Dep. Agric. Ottawa, Ont. (1964).

Turkington, R., et. al., "The Biology of Canadian Weeds. 42. *Stellaria media* (L.) Vill.," *Can. J. Plant Sci.* 60:122-133, Agricultural Institute of Canada (1980) [Reprinted 1984: as pp. 122-133 in The Biology of Canadian Weeds, contributions 33-61. Edited by G.A. Mulligan, Agriculture Canada Publ. No. 1765].

Ullstrup, A.J., "Bacterial Stripe of Corn," *Phytopathology* 50:906-910, American Phytopathological Society (1960).

Vandamme, P., et. al., "Polyphasic Taxonomic Study of the Emended Genus *Arcobacter* with *Acrobacter butzleri* comb. nov. and *Arcobacter skirrowii* sp. nov., and Aerotolerant Bacterium Isolated from Veterinary Speciments," *Int. J. Syst. Bacteriol.* 42:344-356, Society for General Microbiology (1992).

Vandamme, P., et. al., "Occurrence of Multiple Genomovars of *Burkholderia cepacia* in Cystic Fibrosis Patients and Proposal of *Burkholderia multivorans* sp. nov.," *Int. J. Syst. Bacteriol.* 42:1188-1200, Society for General Microbiology (1997).

Vandamme, P., et. al., "Identification and Population Structure of *Burkholderia stabillis* sp. nov. (formerly *Burkholderia cepacia* Genomovar IV)," *J. Clin. Microbiol. 38*:1042-1047, American Society for Microbiology (2000).

Viallard, V., et al., "*Burkholderia graminis* sp. nov., a rhizospheric *Burkholderia* species, and reassessment of [*Pseudomonas*] *phenazinium*, [*Pseudomonas*] *pyrrocinia* and [*Pseudomonas*] *glathei* as *Burkholderia*," *Int. J. Syst. Bacteriol. 48*:549-563, Society for General Microbiology (1998).

Wapshere, A.J., "A strategy for evaluating the safety of organisms for biological weed control," *Ann. Appl. Biol. 77*:201-211, Biochemical Society (1974).

Watson, A.K., "Host Specificity of Plant Pathogens in Biological Weed Control," in *Proceedings of the 6th International Symposium of Biological Control of Weeds*, Aug. 19-25, Delfosse, E.S., ed., Agriculture Canada, Ottawa, Ont., pp. 577-586 (1984).

Watson, A.K., and Wymore, L.A., "Indentifying Limiting Factors in the Biocontrol of Weeds," in *New Directions in Biological Control: Alternatives for Suppressing Agricultural Pests and Diseases*, New York, NY, pp. 305-316 (1990).

Watson, A.K., "Introduction," *Biological Control of Weeds Handbook*, Weed Science Society of America, Champaign, IL, pp. 3-12 (1990).

Watson, A.K., "Registered Bioherbicide Products," *Biological Control of Weeds Handbook*, Weed Science Society of America, Champaign, IL, pp. 173-175 (1993).

Whitford, M.F., et. al., "Phylogentic Analysis of Rumen Bacteria by Comparative Sequence Analysis of Cloned 16S rRNA Genes," *Anaerobe 4*:153-163, Academic Press (1998).

Whitford, M.F., et. al., "Identification of Bacteriocin-Like Inhibitors from Rumen-*Streptococcus* spp. and Isolation and Charterization of Bovicin 255," *Appl. Environ. Microbiol. 67*:569-574, American Society For Microbiology (2001).

Zhang, H., et. al., "*Burkholderia kururiensis* sp. nov., a trichloroethylene (TCE)-degrading bacterium isolated from an aquifer polluted with TCE," *Int. J. Syst. Evol. Microbiol. 50*:743-749, Society for General Microbiology (2000).

Zidack, N.K., et. al., "Promotion of Bacterial Infection of Leaves by an Organosilicone Surfactant: Implications for Biological Weed Control," *Biol. Control 2*:111-117, Academic Press (1992).

CHICKWEED BIOHERBICIDES

This application claims the benefit of priority from Canadian Patent Application No. 2,421,373, filed Mar. 7, 2003, the entire contents of which are incorporated herein by reference.

BACKGROUND OF THE INVENTION

The invention relates to biocontrol agents for suppressing weed growth. More specifically the present invention relates to bacterial biocontrol agents for suppression of weed growth.

Chickweed (*Stellaria media*) is one of the most important weeds in Canada. It is a vigorous competitor for space and nutrients; an aesthetic problem in agricultural crops, market gardens, and urban centers; and listed as a noxious weed in the Noxious Weeds Act of Alberta and Manitoba (Mann et al., 1950; Terkington et al., 1980).

Chickweed is distributed across all Canadian provinces. It is found from Vancouver Island to Newfoundland, and from the United States border to the Mackenzie delta at 69 N (Terkington et al., 1980). Previous data showed that chickweed is more common in B.C. and eastern Canada than in the prairies, however, its populations in the prairie provinces of Canada have been dramatically increasing over the past 10 years. Overall, the relative abundance of chickweed over these years rose by 4, 6, and 17 rankings in Alberta, Saskatchewan and Manitoba, respectively (Thomas et al., 1998). Presently, chickweed is the most abundant weed species in Alberta, followed by wild oats (Thomas et al., 1997).

The main control method is the use of chemical herbicides that belong mainly to Groups 2 and 4. However, herbicide resistance in chickweed to Group-2 herbicides in Canada and Group-4 herbicides in Europe has been reported (Devine et al., 1991; Hall and Devine, 1990; Lutman & Heath, 1990; O'Donovan et al., 1994). Herbicide resistance development in chickweed substantially limits herbicide choices for its control in most crops and other non-agricultural lands such as home gardens and lawns. This situation provides an opportunity to develop "biological herbicide" or "bioherbicide" or "microbial herbicides" for chickweed control.

SUMMARY OF INVENTION

The invention relates to biocontrol agents for suppressing weed growth. More specifically, the present invention relates to bacterial biocontrol agents for suppression of weed growth.

The present invention relates to the development of effective and environmentally safe bioherbicides for biological control of chickweed. More particularly, the present invention (1) provides bioherbicides for the control of plants, such as chickweed, (2) provides methods for producing propagules of the bioherbicide for the control of plants, such as chickweed, and (3) provides methods for controlling the growth of plants, such as chickweed.

The present invention provides the use of a strain of biocontrol agent *Burkholderia andropogonis*, such as *Burkholderia andropogonis*, (Smith 1911) Gillis et al. 1995, comb. nov., deposited under ATCC Accession No. PTA-4234 for controlling or suppressing the growth of a weed. Preferably, the weed belongs to the order Caryophyllales, more preferably the weed is a member of the family Caryophyllaceae, even more preferably the weed is a member of the subfamily Alsinoideae, most preferably the weed is a member of the genus *Stellaria.*

Also provided by the present invention is a biocontrol composition for controlling the growth of a weed, comprising a strain of biocontrol agent *Burkholderia andropogonis*, such as *Burkholderia andropogonis*, (Smith 1911) Gillis et al. 1995, comb. nov., deposited under ATCC Accession No. PTA-4234, and a suitable medium. The acceptable medium may comprise a liquid culture medium, a solid culture medium or a combination thereof. Preferably the acceptable medium is a liquid culture medium. Preferably, the weed belongs to the order Caryophyllales, more preferably the weed is a member of the family Caryophyllaceae, even more preferably the weed is a member of the subfamily Alsinoideae, most preferably the weed is a member of the genus *Stellaria.*

The present invention further provides a biocontrol composition comprising biocontrol agent *Burkholderia andropogonis* (Smith 1911) Gillis et al. 1995, comb. nov., deposited under ATCC Accession No. PTA-4234, and a suitable medium. The present invention also provides the use of the just described composition for controlling or suppressing the growth of a weed. The present invention also provides a method for suppressing weed growth, comprising applying the just described composition to a weed. for controlling or suppressing the growth of a weed, such as a weed belonging to the order Caryophyllales. Preferably, the weed belongs to the order Caryophyllales, more preferably the weed is a member of the family Caryophyllaceae, even more preferably the weed is a member of the subfamily Alsinoideae, most preferably the weed is a member of the genus *Stellaria.*

Also according to the present invention there is provided a method for suppressing weed growth, comprising applying a strain of biocontrol agent *Burkholderia andropogonis*, such as *Burkholderia andropogonis*, (Smith 1911) Gillis et al. 1995, comb. nov., deposited under ATCC Accession No. PTA-4234, to a weed. Preferably, the weed belongs to the order Caryophyllales, more preferably, the weed is a member of the family Caryophyllaceae, even more preferably the weed is a member of the subfamily Alsinoideae, most preferably the weed is a member of the genus *Stellaria.*

The present invention also provides a method of suppressing weeds during crop growth comprising:

a) adding an effective amount of a biocontrol composition comprising a strain of biocontrol agent *Burkholderia andropogonis*, such as *Burkholderia andropogonis* (Smith 1911) Gillis et al. 1995, comb. nov., deposited under ATCC Accession No. PTA-4234, formulated in an acceptable medium, to an area of plants, and;

b) growing said plants.

Preferably, the weed belongs to the order Caryophyllales, more preferably, the weed is a member of the family Caryophyllaceae, even more preferably the weed is a member of the subfamily Alsinoideae, most preferably the weed is a member of the genus *Stellaria.*

The biocontrol agent or biocontrol composition may be applied to weeds by any method known in the art, but is preferably applied by spraying, for example, but not limited to airbrush spraying or broadcast spraying. Broadcast application may be effected using a nozzle, which enhances the reduction of the size of the droplets, which are emitted during application of the biocontrol agent or composition as defined above.

In particular, the present invention relates to the use of the bacterial isolate, CW00B006C, for causing severe disease on chickweed. Typical disease symptoms include chlorosis, resulting in slower chickweed growth and death. Based on phenotypic properties, fatty acid composition, and 16s rDNA sequences, the bacterial strain CW00B006C has been identified as *Burkholderia andropogonis* (Smith 1911) Gillis et al. 1995, comb. nov, and has been deposited under ATCC Accession No. PTA-4234. This bacterium is easily cultured in submerged conditions and its cell production has been characterized using different liquid culture media and various medium pH. Host specificity tests against 36 plant species in 30 genera and 8 families demonstrated that the use of *B. andropogonis* as a bioherbicide for control of chickweed would not cause major concerns to crops and native flora in Canada. Various factors impact the herbicidal performance of this bacterium against chickweed. Under greenhouse conditions, increasing the bacterial cell concentration, repeat application, addition of the surfactant Silwet L-77® at 0.1%–0.2%, or application of bacterial inoculum to chickweed seedlings at an older growth stage, significantly increases disease severity on chickweed seedlings. Under field conditions, about 65%–80% disease severity is consistently observed with application of *B. andropogonis* at $10^9$–$10^{10}$ CFU/ml plus 0.15% Silwet 77®. A maximum percent dry weight reduction of 79.9% under field conditions was obtained. Moreover, *B. andropogonis* causes equivalent disease severity on Group 2 herbicide resistant chickweed seedlings, providing a new approach for mitigating herbicide resistance development in chickweed. Cell-free culture filtrates cause symptoms similar to those caused by the bacterial cells, indicating the potential of using fermentation broth alone, or in combination with bacterial cells, for chickweed control.

This summary does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein.

DETAILED DESCRIPTION OF THE PREFERRED EMBODIMENT

Figure 1:
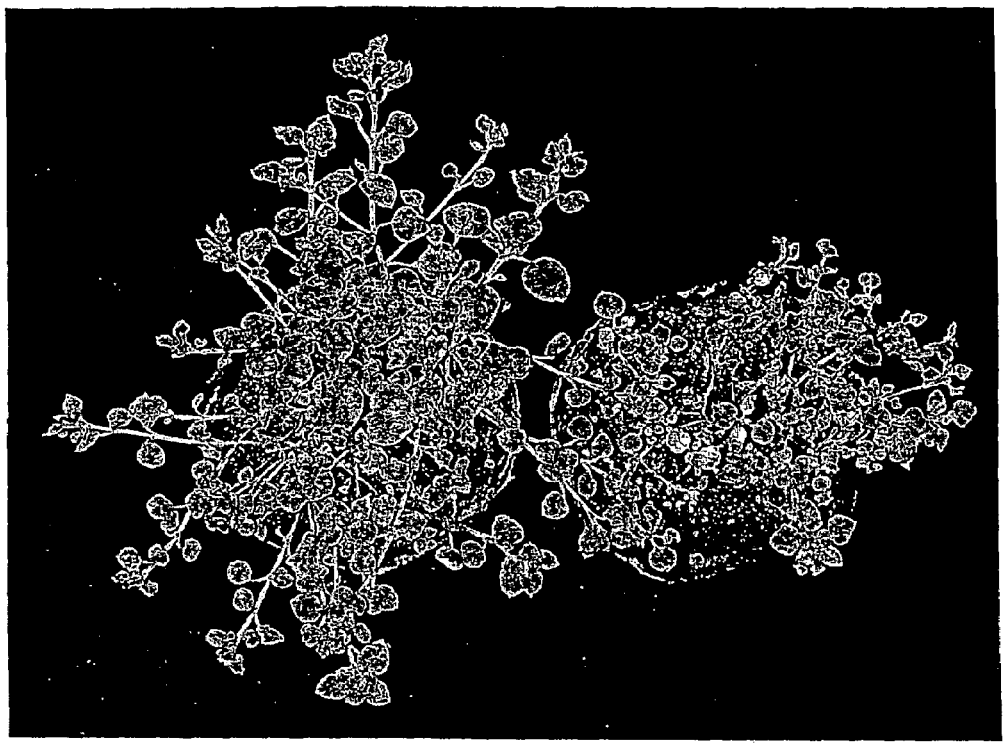
FIG. 1 shows disease symptoms caused by the bacterial isolate CW00B006C in chickweed.

The invention relates to biocontrol agents for suppressing weed growth. More specifically, the present invention relates to bacterial biocontrol agents for suppression of weed growth.

The following description is of a preferred embodiment by way of example only and without limitation to the combination of features necessary for carrying the invention into effect.

By the term "biocontrol agent" is meant a microorganism which suppresses the growth of, or kills, a target pest, for example, but not limited to a plant or a weed. More specifically, the biocontrol agents of the present invention may be used to suppress the growth of one, or more than one target pest. Without wishing to be bound by theory, the biocontrol agent suppresses the growth of a target pest, for example, a plant or weed (i.e. exhibits weed suppressive activity), by interfering with the normal growth and development of the target plant or weed. For example, but not wishing to be limiting, the biocontrol agent may inhibit root growth, shoot growth, reduce biomass, inhibit seed production, reduce competitiveness of the target plant or weed for a crop's water and nutrients, or a combination thereof.

As someone of skill in the art will understand, in order for the biocontrol agent of the present invention to be grown, cultured or used in accordance with the embodiments of the present invention, it is preferable that the biocontrol agent be grown in a suitable medium to produce a biocontrol composition or formulation. By the term "suitable medium" or "acceptable medium" it is meant any liquid, semi-liquid or solid substrate which allows a biocontrol agent such as *Burkholderia andropogonis*, (Smith 1911) Gillis et al. 1995, comb. nov., deposited under ATCC Accession No. PTA-4234, to grow, or to remain viable, or both grow and remain viable. The present invention contemplates a biocontrol composition comprising a bacterial biocontrol agent, such as a strain of *Burkholderia andropogonis*, for example, biocontrol agent *Burkholderia andropogonis*, (Smith 1911) Gillis et al. 1995, comb. nov., deposited under ATCC Accession No. PTA-4234. Preferably, the composition permits an effective amount of the biocontrol agent to remain viable prior to, and after, being applied to a crop.

ATCC Accession No. PTA-4234 was deposited on Apr. 17, 2002. The ATCC is the American Type Culture Collection, P.O. Box 1549, Manassas, Va., 20108, USA.

More preferably, the composition permits the biocontrol agent to remain viable for a period between about 1 day to about 1 month following application of the biocontrol composition of the present invention onto a plant, or soil.

The biocontrol agent or biocontrol composition of the present invention may be applied to plants, soil or both plants and soil. Preferably, the biocontrol agent or composition is applied to plant foliage, for example the foliage of the target weed. Alternatively, the biocontrol agent or composition may be applied directly to soil, either before, during or after seeding a crop. The biocontrol agent may be applied by any method known in the art, for example, but not limited to spraying, pouring, dipping or the like. Preferably, the biocontrol composition of the present invention is applied by spraying.

Therefore, the present invention provides for the use of fungal biocontrol agent *Burkholderia andropogonis*, (Smith 1911) Gillis et al. 1995, comb. nov., deposited under ATCC Accession No. PTA-4234, grown and formulated in a suitable composition for the suppression of weeds. Preferably, the weed belongs to the order Caryophyllales, more preferably, the weed is a member of the family Caryophyllaceae, even more preferably the weed is a member of the subfamily Alsinoideae, most preferably the weed is a member of the genus *Stellaria*.

However, as someone of skill in the art will understand, the amount of the biocontrol composition required for suppression of a weed may be dependent on the medium in which the biocontrol agent is formulated and the method by which it is formulated. For example, but not wishing to be limiting, a formulation and medium which permits a greater percentage of the biocontrol agent to remain viable may require less biocontrol composition to suppress weed growth than does another formulation and medium in which the biocontrol agent is less viable. Further, the amount of a biocontrol composition required for suppression of a weed may be influenced by environmental factors such as but not limited to temperature, humidity, soil pH, and soil type.

Naturally occurring fungi and bacteria were isolated from various locations across Alberta and from Saskatoon. A total of 52 fungal and 25 bacterial isolates with some pathogenicity to chickweed were found after the demonstration of Koch's postulates. Of these isolates, the bacterial isolate, CW00B006C, deposited under ATCC Accession No. PTA-4234, typically causes disease symptom on chickweed of chlorosis and necrosis, resulting in slower plant growth and death. CW00B006C was selected as the bioherbicide candidate for further study. The use of this bacterium as a bioherbicide does not require dew or free moisture to cause the disease.

Based on phenotypic properties, fatty acid composition, and 16s rDNA sequences, the bacterial strain CW00B006C has been identified as *Burkholderia andropogonis* (Smith 1911) Gillis et al. 1995, comb. nov., and deposited under ATCC Accession No. PTA-4234 on Apr. 17, 2002.

This bacterium is easily cultured in submerged conditions. Cell production was significantly affected by the liquid culture media. No lag phase was observed in nutrient glucose broth (NGB), tryptic soy dextrose (TSD), and King's medium B (KB) and about a 2–4 h lag phase was observed in nutrient broth yeast extract (NBY). Exponential growth ended around 22–24 h in all four media tested. Death phase was observed at 42 h in KB and 56 h in NGB and TSD. Growth rate was not significantly different among four media tested, but initial cell production in NBY, NGB, and TSD were similar and significantly greater than that in KB. Estimated generation time (g) was 2.9 h in KB, 2.7 h in NBY, 2.9 h in NGB, and 3.0 in TSD. Medium pH did not affect cell production of *B. andropogonis*. Addition of chickweed extract reduced cell production by 50% when culture time was more than 48 h.

Thirty-six plant species in 30 genera and 8 families, selected by using the centrifugal phylogenetic method, were screened against the bacterial strain *Burkholderia andropogonis* (CW00B006C), a bioherbicide candidate collected in Alberta, Canada from diseased chickweed. Trials were performed under greenhouse conditions. Plants were inoculated with a bacterial suspension at $10^9$–$10^{10}$ CFU/ml plus a surfactant, Silwet L-77®. This bacterial strain of *B. andropogonis* caused disease of host plants distributed in the Caryophyllaceae, Poaceae, and Fabaceae families. The number of species in the Caryophyllaceae family that this bacterial strain was able to infect is relatively wide including chickweed and six other weeds common in western Canada, expanding *B. andropogonis* weed control spectrum as a bioherbicide. In the Poaceae family, corn is susceptible to this strain of bacterium. In the Fabaceae family, hosts of our *B. andropogonis* strain were restricted to Tribe Vicieae containing common vetch and chickpea. The strain of *B. andropogonis* of the present invention is not pathogenic to the majority of major economically important crops cultivated in western Canada. On the basis of host specificity, the use of *B. andropogonis* as a bioherbicide for control of common chickweed will not cause major concerns to crops and native flora in Canada.

Efficacy of chickweed control with *Burkholderia andropogonis* (bacterial isolate CW00B006C) was assessed under both greenhouse and field conditions. Various factors impacted herbicidal performance of this bacterium against chickweed. Under greenhouse conditions, increasing bacterial cell concentration, repeat application, addition of surfactant Silwet L-77® at 0.1%–0.2%, or application of bacterial inoculum to chickweed seedlings at an older growth stage significantly increased disease severity on chickweed seedlings. However, spray pH did not affect the bacterial performance as a bioherbicide against chickweed. Under field conditions, about 65%–80% disease severity was constantly observed with application of *B. andropogonis* at $10^9$–$10^{10}$ CFU/ml plus 0.15% Silwet 77®. A maximum percent dry weight reduction of 79.9% was obtained. Moreover, *B. andropogonis* caused equivalent disease severity on Group 2 herbicide resistant chickweed seedlings, providing a new approach for mitigating herbicide resistance development in chickweed.

Cell-free culture filtrates of *Burkholderia andropogonis* caused symptoms similar to those caused by the bacterial cells, indicating the potential of using fermentation broth alone, or combination with bacterial cells for chickweed control.

The above description is not intended to limit the claimed invention in any manner, furthermore, the discussed combination of features might not be absolutely necessary for the inventive solution.

The present invention will be further illustrated in the following examples. However, it is to be understood that these examples are for illustrative purposes only, and should not be used to limit the scope of the present invention in any manner.

EXAMPLE 1

Collection and Screening of Bioherbicide Candidates for Control of Chickweed

The use of living microorganisms, mainly plant pathogens, for control of weeds has received increasing interest in the last three decades, especially the bioherbicide approach (Charudattan, 2001). The bioherbicide approach. involves three major phases or stages: 1) discovery, 2) development, and 3) deployment (Templeton, 1982). Major activities in the discovery phase involve the collection of diseased plant material, the isolation of causal organisms, and the demonstration of Koch's postulates (Watson, 1993). To date, there has been no research to extensively search for chickweed diseases with an aim to develop a bioherbicide.

Unlike the classical biological control approach, the bioherbicide approach usually relies on the use of endemic pathogens (Watson, 1993). In Canada, three fungi, *Septoria stellariae* Ro. & Desm., *Melampsorella caryophyllacearum* Schroet., and *Puccinia arenariae* (Schum.) Wint., were associated with chickweed (Conners, 1967; Tom, 1964). But it is unknown whether these fungi can be isolated and used as bioherbicide candidates. In addition, the existence of other fungi and bacteria that infect chickweed and possess potential as bioherbicides remains unknown.

In this example, diseased chickweed plants are collected, causal microorganisms are isolated, and pathogenic fungi-and bacteria are identified with bioherbicide potential.

Collection and Isolation of Fungi and Bacteria

Collection of Diseased Chickweed.

Several field trips were made from May to September in 1999 and 2000 to collect diseased chickweed plant materials from agricultural crops and market gardens in the districts of Vegreville, Tofield, Busby, Ryley, Ranfurly, Fort Assiniboine, Lamont, Spruce Grove, Leduc, Red Deer, Calgary, Edmonton, and Saskatoon. Diseased plant parts of chickweed were collected, cut to appropriate size, and transported at 4° C.

Isolation of Causal Organisms.

Isolation was carried out in the lab within 24 h of field collection in order to keep the samples as fresh as possible. Diseased plant material was sorted based on whether fungal or bacterial disease was most likely to have caused disease symptoms. To isolate fungi, leaf, stem or root pieces with lesions were surface sterilized with 0.5% sodium hypochlorite solution and incubated on fresh potato dextrose agar (PDA; Difco, Detroit, Mich.). Fungi that grew from the lesions were isolated. For all isolated fungi, single cell colonies were obtained by using standard single spore or hyphal tip techniques to ensure species purity (Tuite, 1969).

To isolate bacteria, pieces of leaves or stems with lesions were washed with running tap water, placed into a drop of sterile distilled water, and macerated. A loopfull of the macerated solution was streaked across a plate of nutrient agar, nutrient glucose agar, and nutrient broth yeast extract agar (Schaad, 1988). Single, morphologically distinct bacterial colonies were then selected from culture plates after 4–7 days and streaked on a fresh plate of culture media to obtain pure cultures.

Maintenance of Microorganisms.

A 15% glycerol solution was prepared as follows: Fifteen ml of glycerol was added to 85 ml of distilled water, the resulting mixture was then autoclaved and cooled to room temperature. Then, 1.8 ml of 15% glycerol solution was dispensed into 2 ml cryovials. A pure culture of fungi or bacteria was scraped with a scalpel blade and placed in each of 3 cryovials of glycerol solution. Cryovials of samples were placed in a Mr. Frosty (Nalgene Cryo Freezing container, Cat No 5100-0001) in a freezer at −80° C. for a minimum time of 85 minutes to freeze at a rate of 1° C. per minute to −80° C. Frozen samples were then placed in racks for storage at −80° C. as stock cultures.

Screening of Fungi and Bacteria

Inoculum Preparation

For fungal pathogens, a cryovial of stock culture was warmed to room temperature in a 36° C. water bath and the contents were dispensed in 200 µl aliquots on the surface of potato dextrose agar (PDA) plates, and spread with a sterile glass rod. The PDA plate was incubated for 5 days at 22° C. under 12 h light provided by two, 20 W, 60 cm long cool white fluorescent tubes placed 30 cm above the PDA plates. Single-spore colonies were then made for all fungal isolates using standard single-spore-technique and cultures were incubated under conditions as described above. Sufficient spores for experiments were produced by transferring spores from a single-cell colony onto several PDA plates (spread plates). Plates were incubated as above for 1–2 wks. Spores were harvested by gently scraping the surface of the agar and transferring into sterilized distilled water. Spore concentrations were determined using a haemocytometer.

For bacterial pathogens, a cryovial of stock culture was warmed to room temperature in a 36° C. water bath. A 50 µl aliquot of suspension from the vial was added to each 18×150 mm glass test tube containing 3 ml nutrient glucose broth (NGB) at a pH of 6.8. The test tubes were incubated on an orbit shaker at 200 rpm for 24–72 h under ambient laboratory conditions (24° C.±3). Contents of tubes were used as 'seed inoculum'. The bacterial culture for inoculations was produced by placing 75 ml of NGB (pH 6.8) in each 250-ml Erlenmeyer flasks, autoclaving, cooling, inoculating with 1 ml per flask of the 'seed inoculum', and incubating flasks on an orbit shaker at 200 rpm for 24–72 h under ambient laboratory conditions (24° C.±3). About 30 ml of cell suspension from each flask was then placed in a 50 ml centrifuge tube and centrifuged 10 minutes at 3700 rcf (Sorvall RC-5B refrigerated superspeed centrifuge). Supernatant was poured from each tube and the bacterial pellet was resuspended in 20 ml of 0.01 M, pH 7 phosphate buffer. Viable bacterial cell production was determined using the dilution plate count method. Serial dilutions (10×) were performed in dilution tubes containing 9 ml of sterile 0.01 M phosphate buffer, pH 7, and 100 µl of three appropriate dilutions were spread plated on nutrient glucose agar (NGA). Plates were incubated under ambient laboratory conditions for about 4 days. Colony forming units (CFU) per ml were determined by counting colonies on plates with 10–200 CFU per plate.

Plant Production

Fungal or bacterial virulence against chickweed was assessed using a single batch of chickweed seeds for all experiments. Seeds were sown in 10-cm-diameter pots filled with pre-prepared soil mix. The soil mix consisted of 140 L soil (loam, pH 6.7, 42% sand, 40% silt, and 18% clay), 107 L sand, 160 L Sunshine Growing Mix (SunGro Horticulture, Bellevue, Wash.), 62 L Fibrous Blond Shagnum Peat Moss (Premier Pro Moss, Riviere-du-Loup, Quebec), 113 L vermiculite (Therm-O-Rock, Chandler, Ariz.), 230 g dolomite lime, and 150 g Super Phosphate (0-45-0) per batch of soil. Seeded pots were placed in a greenhouse with 23/20±4° C. day/night temperature, a 16 h photoperiod, an average light intensity of 300 $\mu Em^{-1}$, and an average relative humidity of 45–50%. After germination, seedlings were thinned to five plants per pot.

Inoculation Procedure

For fungal pathogens, chickweed seedlings at the 4- to 6-leaf stage were inoculated with $5 \times 10^5$ to $5 \times 10^6$ spores/ml to run-off with 0.05% gelatin as a wetting agent, using an airbrush at 100 kPa. Unless otherwise indicated, after spraying, pots were placed in a dark dew chamber with 100% relative humidity at 22° C. for 48h. Subsequently, pots were transferred back to the greenhouse with conditions as mentioned above. Control treatments were sprayed with distilled water containing only the wetting agent.

For bacterial pathogens, chickweed seedlings at the 4- to 6-leaf stage were inoculated with $10^7$–$10^{10}$ CFU/ml of bacterial cells suspended in 0.01 M, pH 7 phosphate buffer plus 0.1% Silwet L-77® (wetting agent) using a airbrush at 100 kPa until all leaf surfaces were evenly wet. Immediately after spraying, pots were returned to the greenhouse. Control treatments were sprayed with 0.01 M phosphate buffer containing only the wetting agent.

Pathogenicity and Virulence to Chickweed

Fungal or bacterial virulence on chickweed were assessed 7 and 14 days after inoculation using a 0 to 3 scale (0—no symptom, 1—light infection, 2—moderate infection, and 3—severe infection to death). For each isolate tested, there were three replications arranged in a completely randomized design. The experiments were repeated at least once.

Disease Symptoms of CW00B006C in Chickweed

To characterize the typical symptoms associated with chickweed disease caused by isolate CW00B006C, chickweed plants inoculated with the bacterium in various greenhouse and field experiments were observed from the onset of symptoms for a three week period after spraying. Symptoms from the various experiments were recorded, compared, and summarized.

Collection and Isolation of Fungi and Bacteria

From 13 different locations, a total of 153 fungal isolates and 448 bacterial strains were isolated from chickweed and stored at −80° C. (Table 1). The findings in this study demonstrated that endemic fungi and bacteria associated with chickweed are much more common than previously reported (Conners, 1967; Toms, 1964). These naturally occurring fungi and bacteria provided a sound base for searching for a bioherbicide candidate.

TABLE 1

Number of fungi and bacteria isolated from chickweed at various locations

| Location | No. Of Isolates Fungi | Bacterial |
|---|---|---|
| Vegreville | 35 | 10 |
| Tofield | 11 | 21 |
| Busby | 10 | 34 |
| Ryley | 1 | 6 |
| Ranfurly | 46 | |
| Fort Assiniboine | 2 | 47 |
| Lamont | 6 | |
| Spruce Grove | 9 | 95 |
| Leduc | 1 | 10 |
| Red Deer | | 206 |
| Calgary | | 16 |
| Saskatoon | 32 | 3 |

Screening of Fungi and Bacteria.

A total of 52 fungal and 25 bacterial isolates with some pathogenicity to chickweed were found (Table 2 and Table 3). Of these isolates, only three fungi and one bacterium are highly pathogenic to chickweed and thus deserve consideration as bioherbicide candidates.

TABLE 2

Virulence of fungal isolates on chickweed (Stellaria media)*

| | |
|---|---|
| Isolates tested | 153 |
| Non-pathogenic isolates | 101 |
| Pathogenic isolates | |
| Slight infection (+) | 46 |
| Moderate infection (++) | 3 |
| Severe infection (+++) | 3 |
| Bioherbicide prospects | 1 |

*Seedlings of chickweed at the 4- to 6-leaf stage were inoculated with $10^5$ to 1 d spores/ml, placed in a dew chamber at 22° C. for 48 h and subsequently maintained in a greenhouse. Pathogenicity and virulence was rated 7 days after inoculation using a 0 to 3 grading system where 0 = noinfection, + = light infection, ++ = moderate infection, and +++ severe infection to death.

TABLE 3

Virulence of bacterial isolates on chickweed (Stellaria media)*

| | |
|---|---|
| Isolates tested | 448 |
| Non-pathogenic isolates | 382 |
| Pathogenic isolates | |
| Slight infection (+) | 58 |
| Moderate infection (++) | 7 |
| Severe infection (+++) | 1 |
| Bioherbicide prospects | 1 |

*Seedlings of chickweed at the 4- to 6-leaf stage were inoculated with $10^7$ to $10^{10}$ CFU/ml and subsequently maintained in a greenhouse. Pathogenicity and virulence was rated 14 days after inoculation using a 0 to 3 grading system where 0 = no infection, + = lightinfection, ++ = moderate infection, and +++ = severe infection to death.

Fungal isolate CW98-235 was the most virulent of the fungal isolates (data not shown). All three fungi, however, required a prolonged dew period (48 h) to cause infection, while the bacterium required no free moisture and had excellent virulence against chickweed. Thus, the bacterial isolate, CW00B006C, was selected as the bioherbicide candidate for further study.

Disease Symptoms of CW00B006C in Chickweed

Figure 2:
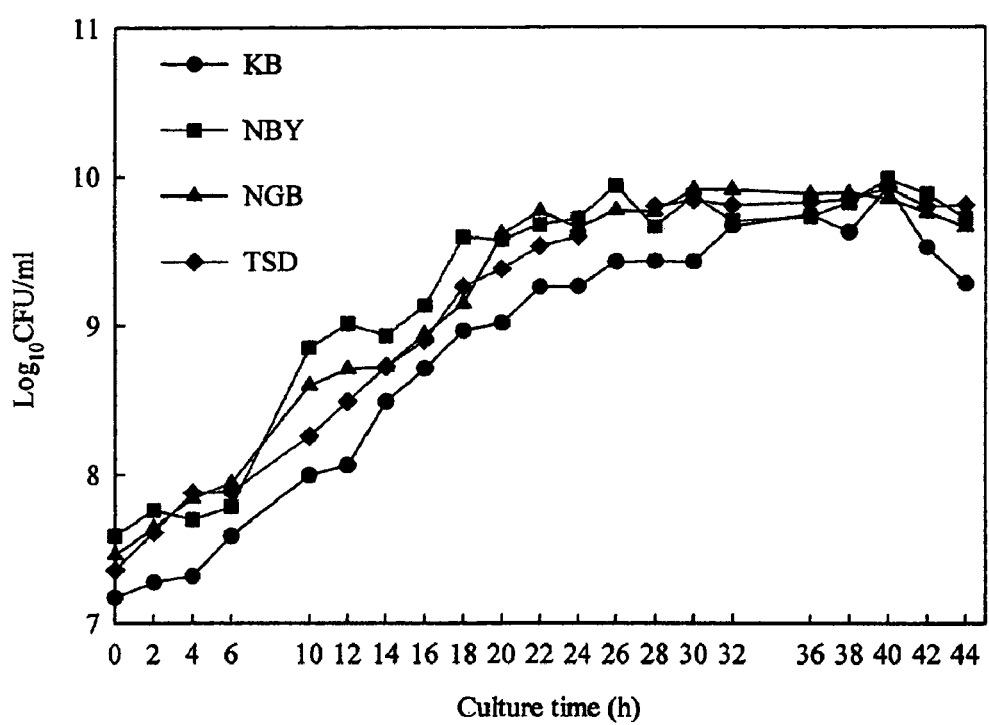
FIG. 2 shows a CW00B006C bacterial cell growth curve in four different liquid culture media over a 44 h period. KB—King's medium B, NBY—nutrient broth yeast extract, NGB—nutrient glucose broth, TSD—tryptic soy dextrose.

Isolate CW00B006C infection of chickweed causes chlorosis on treated leaves and stems, sometimes with necrotic lesions, within 5–7 days after bacterial treatment (FIG. 2.1). As the disease progress, plant growth dramatically slows down. Existing leaves and stem senesce. Emerging leaves were chlorotic and small. Severe infections caused plant death.

Bacteria have excellent potential as weed biocontrol agents because they can be delivered into the xylem via stomata and other natural plant openings with the aid of a new type of surfactant—nonionic organosilicone surfactants (e.g. Silwet 77°) (Zidack et al., 1992; Johnson et al., 1996). As a result, the bacteria do not require a prolonged dew period or free moisture for infection and colonization that are rarely met under field conditions, especially in western Canada. This is a significant advantage over the use of a fungus as a bioherbicide. Therefore, the bacterial isolate CW00B006C possesses great potential as a bioherbicide.

EXAMPLE 2

Characterization and Identification of Bacterium CW00B006C

The native bacterium, strain CW00B006C, caused severe disease on chickweed. In order to further evaluate and develop this bacterium as a bioherbicide, its identification was conducted to provide information on its pathogenicity, culture conditions, and phylogenetic relations. Various techniques are available for bacterial identification including phenotypic and genotypic analyses (Bagsic-Opulencia et al., 2001; Viallard et al., 1998; Whitford et al., 2001). The bacterium was identified using those available technologies including physiological and biochemical characterization, fatty acid composition, and 16s rDNA sequence. In addition, the bacterial growth and disease symptoms were also characterized.

Phenotypic Analyses

The bacterial isolate CW00B006C was characterized and identified based on phenotypic properties including physiological and biochemical characterization and fatty acid composition.

Physiological and Biochemical Characterization

Characterization included gram staining, motility, carbon substrate assimilation, oxidase and other physiological activities using previously described methods (Coeyne et al. 1999; Viallard et al. 1998; Hu et at. 1991). Carbon substrate assimilation tests were performed using auxanographic API 50CH strips (bioMerieux) as recommended by the manufacturer.

Fatty Acid Composition (MIDI-FAME)

The bacterial isolate CW00B006C was grown overnight at 27° C. on trypticase soy agar and harvested for extraction of total cellular fatty acids. Total cellular fatty acids were extracted and methylated for fatty acid methyl ester (FAME) analysis by gas chromatography (Paisley 1996; Vandamme et al. 1992) and the profiles compared with a computerized database using Sherlock microbial identification system software (MIDI, Newark, Del.).

Genotypic Analyses (16S rDNA Sequence)

Genomic DNA was prepared from bacterial isolate CW00B006C as described by Whitford et al. (1998). 16S ribosomal rRNA genes (rDNA) were amplified using primers FP1 [5'AGA GTT YGA TYC TGG CT 3' (SEQ ID NO:1)] and R1492 [5'-TAC GGY TAC CTT GTT ACG ACT-3' (SEQ ID NO:2)] based on primers described by Lane (1991). Primers and PCR reaction conditions have been previously described (Whitford et al., 2001). The 16S rDNA PCR products were purified using a QlAquick PCR purification kit (QIAGEN) and the recovered PCR products were quantified using a DyNAQuant 200 Fluorometer (Hoefer). The PCR products were directly sequenced using a Thermo Sequenase cycle sequencing kit (Amersham Pharmacia Biotech) using IRD800-labeled M13 forward and reverse primers (LI-COR Inc., Lincoln, Nebr.), plus the IRD800-labeled 16S rDNA specific primers FP1, EUB338f [5'-ACT CCT ACG GCA GGC AG-3' (SEQ ID NO:3)], 519r [5'-GWA TTA CCG CGG CKG CTG-3' (SEQ ID NO:4)], 926f [5'-AAA CTY AAA KGA ATT GAC GG-3' (SEQ ID NO:5)], 1100r [5'-AGG GTT GCG CTC GTT G-3' (SEQ ID NO:6)], and 1492r. Sequence products were analyzed on a LI-COR model 4000L sequencer. Sequence fragments were assembled and edited using Sequencher version 3.1 (Gene Codes Corp., Ann Arbor, Mich.). The resulting sequence was analyzed using the Similarity Matrix Program at the Ribosomal Database Project II (RDPII; rdp.cme.msu.edu/html/).

Phenotypic Analyses

Physiological and Biochemical Characterization

Isolate CW00B006C is a motile, gram negative rod, 0.5×1.5–2.5 µm, that grows only aerobically without production of any soluble or fluorescent pigments. The isolate has urease activity, utilizes citrate and produces poly-13-hydroxybutyrate. The isolate does not produce indole or have oxidase, arginine and lysine dihydrolase, gelatin liquification, lecithinase, (3-galactosidase and I3-glucouronidase activities. The isolate grows well at 30° C. but not at 37° C. or higher. Tests based on the assimilation of 49 carbon sources exhibited that isolate CW00B006C utilizes 20 carbons as a sole carbon source (Table 4). Isolate CW00B006C matches closely to *Burkholderia andropogonis* (Smith 1911) Gillis et al. 1995, comb. Nov., differing in its utilization of D-xylose but not gluconate (Hu et al. 1991; Gillis et al., 1995; Viallard et al. 1998).

TABLE 4

Carbon assimilation of CW00B006C as opposed to type strain of *Burkholderia andropogonis*

|  | CW00B006C | *Burkholderia andropogonis* |
|---|---|---|
| Glycerol | + | + |
| D-arabinose | + | + |
| L-arabinose | + | + |
| Ribose | + | + |
| D-xylose | + | − |
| Adonitol | + | + |
| Galactose | + | + |
| D-glucose | + | + |
| D-fructose | + | + |
| D-mannose | + | + |
| Rhamnose | + | V |
| Inositol | + | + |
| Mannitol | + | + |
| Sorbitol | + | + |
| Lactose | + | + |
| Trehalose | + | V |
| D-raffinose | + | V |
| D-lyxose | + | + |
| D-fucose | + | V |
| D-arabitol | + | + |
| Gluconate | − | + |

TABLE 4-continued

Carbon assimilation of CW00B006C as opposed to type strain of Burkholderia andropogonis

| | CW00B006C | Burkholderia andropogonis |
|---|---|---|
| Erythitol | – | – |
| L-xylose | – | – |
| β-methyl-xyloside | – | – |
| L-sorbose | – | – |
| Dulcitol | – | – |
| α-methyl-D-mannoside | – | – |
| α-methyl-D-glucoside | – | – |
| N-acetyl-glucosamine | – | – |
| Amygdalin | – | – |
| Arbutine | – | – |
| Aesculin hydrolysis | – | – |
| Salicin | – | – |
| Cellobiose | V | – |
| Maltose | V | – |
| Melibiose | – | – |
| Sucrose | – | – |
| Inulin | – | – |
| Melezitose | – | – |
| Starch | – | – |
| Glycogen | – | – |
| Xylitol | – | – |
| β-gentibiose | V | – |
| D-turanose | – | – |
| D-tagatose | – | – |
| L-fucose | – | – |
| L-arabitol | – | – |
| 2-ketogluconate | – | V |
| 5-ketogluconate | – | – |

*Data on B. andropogonis were based on Viallard et al. (1998) and Hu et al. (1991)

Fatty Acid Composition

The main fatty acids (>1%) in the cells of strain CW00B006C are 14:0 (6.1%), 16:0 (14.2%), 18:16)7c (22.4%), 16:1 2-OH (4.6%), 16:0 2-OH (5.7%), 16:0 3-OH (4.5%), 18:1 2-OH (2.2%), 17:0 cyclo (5.2%), 19:0 cyclo w8c (7.1%), summed feature 2 (14:0 3-OH; 4.5%) and summed feature 3 (16:1w7c; 21.5%). These results match published values for B. andropogonis (Coeyne et al., 2001 a; Stead, 1992). In particular, the presence of 14:0 3-OH, 16:1 2-OH, 16:0 2-OH and 16:0 3-OH and no other hydroxy fatty acids are indicative of Burkholderia sp. (Stead, 1992). Further, the predominance of 16:0, 18:1ω7c and summed feature 3 are indicative of B. andropogonis (Coeyne et al., 2001a; Coeyne et al., 2001b; Coeyne et al., 2001c; Vandamme et al., 1997; Vandamme et al., 2000; Zhang et al.,2000).

Genotypic Analyses (16S rDNA Sequencing)

A 1408 base pair sequencing product was produced from amplification of the rDNA from isolate CW00B006C. The 16S rDNA sequence of isolate CW00B006C is very similar to that of Burkholderia andropogonis ATCC 19311 (formerly Pseudomonas woodsii; similarity value 98.6%) and Burkholderia andropogonis ATCC 23061$^T$. Therefore, genotypic analyses confirmed the identification of isolate CW00B006C as B. andropogonis (Smith 1911) Gillis et al. 1995, comb. nov.

EXAMPLE 3

Chapter 4 Cell Production of Bacterium CW00B006C

The development of low-cost methods for mass production of a bioherbicide is an important step for the commercialization of a bioherbicide (Stowell et al., 1989; Boyette et al., 1991). Submerged liquid culture spore production is the preferred technique for mass production of biocontrol agents because the technology is readily available and the scale-up process from the research phase to the development phase is relatively easy (Churchill, 1982; Stowell et al., 1989; Jackson, 1997). So far, no information has been reported on submerged liquid culture cell production for Burkholderia andropogonis. In this example, the growth curve of B. andropogonis was characterized in different liquid culture media, the effect of medium pH on cell production of B. andropogonis was determined, and (3) the effect of addition of chickweed extracts on cell production of B. andropogonis was evaluated.

For all experiments, stock cultures of CW00B006C were stored in 15% glycerol at −80° C. A cryovial of stock culture was warmed to room temperature in a 36° C. water bath. A 50 µl aliquot of suspension from the vial was added to 18×150 mm glass test tube containing 3 ml of appropriate broth. Test tubes were incubated on an orbit shaker at 200 rpm for 24 h under ambient laboratory conditions (24° C.±3). Contents of tubes of the same medium were combined to produce 'seed inoculum'. Replicate 500 ml flasks of each medium were inoculated with 1 ml of the appropriate 'seed inoculum'. Flasks were placed on an orbit shaker at 200 rpm under ambient laboratory conditions (24° C.±3). Viable bacterial cell production was determined using the dilution plate count method. Serial dilutions (10×) were performed in dilution tubes containing 9 ml of sterile 0.01 M phosphate buffer, pH 7, and 100 µl of three appropriate dilutions were spread plated on nutrient glucose agar (NGA). Plates were incubated under ambient laboratory conditions for about 4 days. Colony forming units (CFU) per ml was determined by counting colonies on plates with 10–600 CFU per plate.

Growth Curve of the Bacterium in Different Liquid Culture Media

The growth of the bacterium in four different liquid culture media was assessed over a 44 h period. Liquid culture medium tested included nutrient glucose broth (NGB; 8 g nutrient broth (Difco), 2.5 g glucose, 1 L distilled water), nutrient broth yeast extract (NBY; 8 g nutrient broth (Difco), 2 g yeast extract (Difco), 2 g $K_2HPO_4$ 0.5 g $KH_2PO_4$, 2.5 g glucose, 1 L distilled water), King's medium B (KB; 20 g proteose peptone #3 (Difco), 1.5 g. $K_2HPO_4$, 1.5 g $MgSO_4.7H_2O$, 15 ml glycerol, 1 L distilled water), and tryptic soy dextrose (TSD; 17 g Bacto tryptone (Difco), 3 g Bacto Soytone (Difco), 5 g NaCl, 2.5 g $K_2HPO_4$, 2.5 g glucose, 1 L distilled water). Two replicate 500 ml flasks of each medium were inoculated with 1 ml of the appropriate 'seed inoculum'. A 0.5 ml sample from each of the two replicate flasks was taken at 0, 2, 4, 6, 10, 12, 14, 16, 18, 20, 22, 24, 26, 28, 30, 32, 36, 38, 40, 42 and 44 h after inoculation. The 2–0.5 ml samples from each medium were combined and viable bacterial cell concentration was determined using the dilution plate count method.

Since the death phase were not observed within 44 h culture time, an extension of culture time to 64 h was used to culture CW00B006C in NGB and TSD. Two trials were conducted. For each trial, 3 replicate 500 ml flasks of each medium were inoculated with 1 ml of appropriate 'seed inoculum'. A 1 ml sample from each replicate flask was taken every 4 hours from 0 to 44 hrs in trial 1 and from 0 to 48 hours in trial 2, and at 56 and 64 hours for both trials. Each sample was separately analyzed using the dilution plate count method to determine viable bacterial cell concentration. Data from the two trials of each experiment were pooled because the variances of trials were homogeneous according to Bartlett's test (Gomez & Gomez, 1984).

Effect of Medium pH on Bacterial Cell Production

A cryovial of stock culture was warmed to room temperature in a 36° C. water bath. A 50 µl aliquot of suspension from the vial was added to each 15 mm glass test tube containing 3 ml nutrient glucose broth (NGB) at a pH of 6.8. The test tubes were incubated on an orbit shaker at 200 rpm for 24 h under ambient laboratory conditions (24° C.±3). Contents of tubes were used as 'seed inoculum'. The pH of NGB flasks was adjusted using 1 N HC 1 or NaOH to achieve pHs from 6 to 8 at increments of 0.2 prior to sterilization. Two replicate flasks of each treatment were inoculated with the 'seed inoculum' and incubated on an orbit shaker at 200 rpm for 24 h under ambient laboratory conditions (24° C.±3). Medium pH of each flask after 24 h culture was measured and compared to the original pH. Bacterial cell production was then determined.

Effect of Growth Medium Modification with Chickweed Extracts.

For all experiments, nutrient glucose broth (NGB) at a pH of 6.8 was used as a control treatment to compare the cell production in chickweed extract medium (CWE). To prepare chickweed extract medium, 3–5 wk old chickweed foliage was harvested from the greenhouse and stored at −20° C. until use. Using liquid nitrogen and a pestle and mortar, tissue was crushed to a powder, and combined with an equal amount of distilled water (w/v) to form thick slurry. The slurry was filtered through 2-ply cheesecloth, filtrate was centrifuged at 18500 rcf (Eppendorf 5810R centrifuge) for 15 minutes, supernatant was filter sterilized using a 0.22 µm bottle-top vacuum filter, and resulting sterile CWE medium was stored at 4° C. until use. Stock cultures of isolate CW00B006C were stored in 15% glycerol at −80° C. For each experiment, a cryovial of stock culture was warmed to room temperature in a 36° C. water bath. A 50 µl aliquot of suspension from the vial was added to each 18×150 mm glass test tube containing 3 ml of appropriate medium. The test tubes were incubated on an orbit shaker at 200 rpm for 24 h under ambient laboratory conditions (24° C.±3). Contents of tubes were used as 'seed inoculum'. The bacterial culture for inoculations was produced using 75 ml of sterile NGB or CWE in 250-ml Erlenmeyer flasks inoculated with 0.5 ml per flask of the appropriate 'seed inoculum'. Unless otherwise indicated, flasks were incubated on an orbit shaker at 200 rpm for 24 h under ambient laboratory conditions (24° C.±3). When stated, viable bacterial cell production was determined using the dilution plate count method. Serial dilutions (10×) were performed in dilution tubes containing 9 ml of sterile 0.01 M phosphate buffer, pH 7, and 100 µl of three appropriate dilutions were spread plated on nutrient glucose agar (NGA). Plates were incubated under ambient laboratory conditions for about 4 days. Colony forming units (CFU) per ml was determined by counting colonies on plates with 10–200 CFU per plate.

Growth Curve of the Bacterium in Four Different Liquid Culture Media

Figure 3:
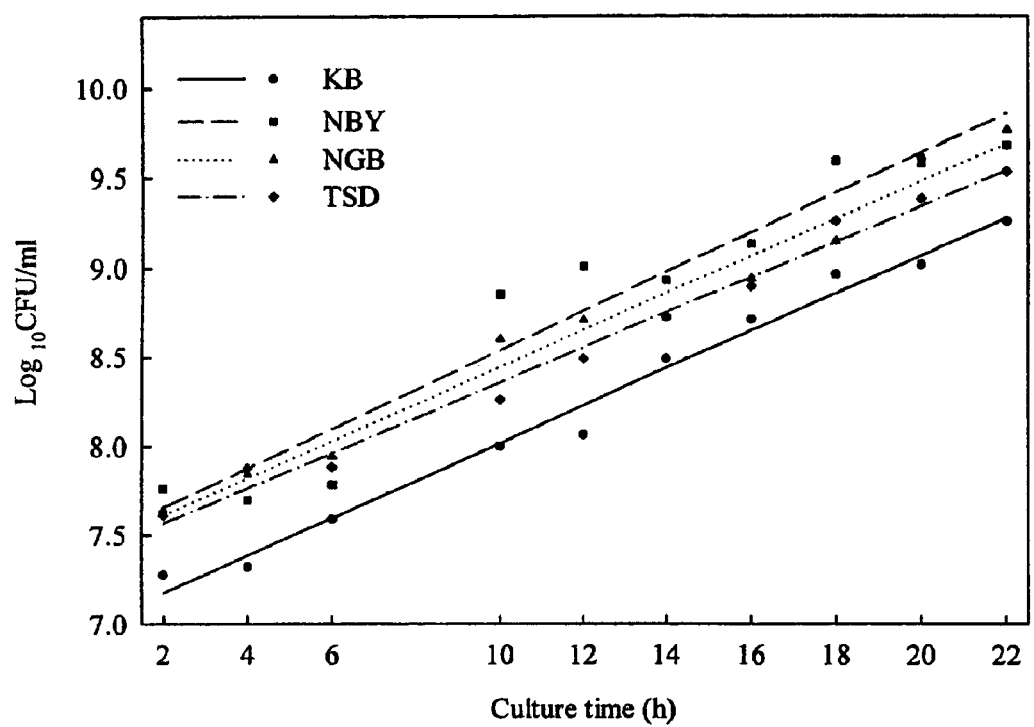
FIG. 3 shows the exponential growth of CW00B006C bacterial cells in four different liquid culture media from 2 to 22–44 h. KB—King's medium B, NBY—nutrient broth yeast extract, NGB—nutrient glucose broth, TSD—tryptic soy dextrose. The best regression equation between cell numbers (N) and time (T) are: (a) For KB, $N=6.968+0.105T$, $r^2=0.9868$, (b) For NBY, $N=7.437+0.110T$, $r^2=0.9317$, (c) For NGB, $N=7.407+0.104T$, $r^2=0.9762$, and (d) For TSD, $N=7.372+0.099T$, $r^2=0.9873$.

Isolate CW00B006C grew well on all four media tested (FIG. 2). No lag phase was observed on NGB, TSD, and KB and about a 2–4 h lag phase was observed on NBY. Exponential growth ended around 22–24 h on all four media tested. Simulation of the exponential growth during this period indicates initial cell production on NBY, NGB, and TSD were similar but significantly greater than that on KB (FIG. 3; Table 5). However, growth rate was not significantly different among the four media tested. Generations of 6.6, 6.4, 7.1, and 6.4 from 2 h to 22 h were observed in KB, NBY, NGB, and TSD, respectively. Estimated generation time (g) was 2.9 h in KB, 2.7 h in NBY, 2.9 h in NGB, and 3.0 in TSD. The stationary phase in all four media tested began at 22–24 h and extended to the end of the testing period at 44 h for NBY, NGB and TSD. Death phase was observed only on KB at 42 h.

Figure 4:
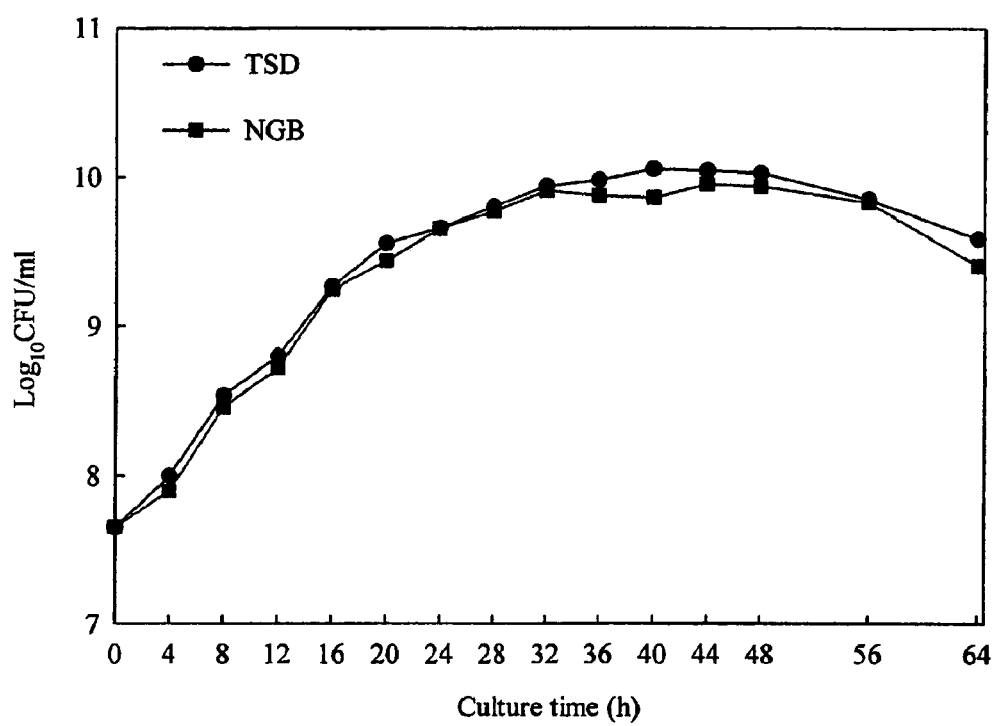
FIG. 4 shows a CW00B006C bacterial cell growth curve in two different liquid culture media over 64 h period. NGB—nutrient glucose broth, TSD—tryptic soy dextrose. Data from the two trials of each experiment were pooled because the variances of trials were homogeneous according to Bartlett's test (Gomez & Gomez, 1984). Data points represent means of six replications.
Figure 5:
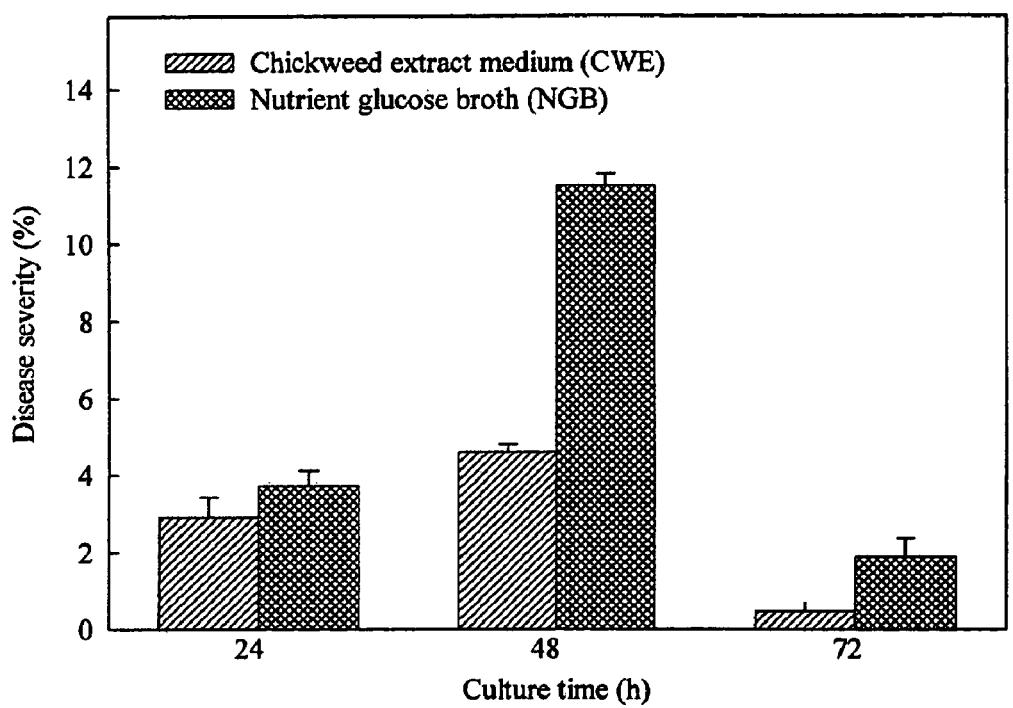
FIG. 5 shows the effect of chickweed extract on CW00B006C bacterial cell production.

Since the death phase were not observed within 44 h culture time, an extension of culture time to 64 h was used to culture CW00B006C in NGB and TSD. Results demonstrated that the growth curve of CW00B006C in both media follows a similar pattern. The death phase began at 56 h (FIG. 4).

TABLE 5

Comparison of exponential growth parameters of CW00B006C among four liquid culture media*

| Medium | Interception** | Slope** | Generation time g |
|---|---|---|---|
| King's medium B | 6.968 b | 0.105 a | 2.87 |
| Nutrient broth yeast extract | 7.437 a | 0.110 a | 2.74 |
| Nutrient glucose broth | 7.407 a | 0.104 a | 2.89 |
| Tryptic soy dextrose | 7.372 a | 0.099 a | 3.04 |

*Cell numbers from 2 h to 22 h were used to do the regression between cell numbers and culture times.
**Values in each column sharing the same letter are not significantly different according to the t-test.

Effect of Medium pH on Bacterial Cell Production Medium pH did not significantly affect the growth curve of isolate CW00B006C, or the bacterial cell production. A slight decrease in cell production was observed with an increase in pH. The highest number of bacterial cells, $9.2 \times 10^{10}$ CFU/ml, was produced at a pH of 6 while the lowest number of bacterial cells, $2.9 \times 10^{10}$ CFU/ml, was produced at a pH of 8.

Effect of Growth Medium Modification with Chickweed Extracts

Since the addition of chickweed extract in culture medium enhanced the efficacy of *B. andropogonis* for the control of chickweed, the bacterial cell production was assessed in the culture medium modified with the chickweed extract (FIG. 4.4). Cell production in CWE was similar to NGB within 24 h. However, when culture time extended to 48 h or 72 h, cell production in CWE was half of that in NGB. Further study is required to balance the cell production and weed control efficacy.

EXAMPLE 4

Host Range

Host specificity of a biocontrol agent is an important factor to consider in a biological weed control program (Watson, 1985). Before using a biological control agent in the field, its host specificity to non-target economic and wild plants must be characterized (Wapshere, 1974).

Various plant species were reported as hosts of *B. andropogonis*. However, cross inoculation studies demonstrated variations in the host reactions of isolates from a particular host genus or species, indicating a degree of host specialization associated with *B. andropogonis* strains (Moffett et al., 1986). According to Moffett et al. (1986), common hosts of *B. andropogonis* include sorghum (*Sorghum bicolor*) and corn (*Zea mays*) of the family Poaceae, common vetch (*Vicia sativa*) of the family Fabaceae, and carnation (*Dian-* thus caryophyllus) and baby's breath (*Gypsophila paniculata*) of the family Caryophyllaceae. Other possible hosts, depending upon the strain, included sudan grass (*Sorghum sudanens*) of the family Poaceae, chick pea (*Cicer arietinum*), velvet bean (*Mucuna deeringiana*), white clover (*Trifolium repens*), and red clover (*Trifolium pratense*) of the family Fabaceae, blueberry (*Vaccinium* sp.) of the family Rubiaceae, and tulip (*Tulip sylvestris*) of the family Liliaceae (Burkholder, 1957; Allen et al., 1970; Goto and Starr, 1971; Hayward, 1972; Nishiyama et al., 1979; Caruso, 1984).

*Burkholderia andropogonis* has never been reported as a crop pathogen in Canada (Howard et al., 1994; Martens et al., 1994). In this example, the host range of this strain of *B. andropogonis* was determined based on the phylogenetic method and the potential risks involved in its use was estimated as a biological control agent of common chickweed in western Canada.

The Organisms

The Target Weeds: Common Chickweed

Common chickweed is native to Europe (Hohm et al., 1977; Turkinton et al., 1980). It is believed to be one of the 12 most successful colonizing species among the noncultivated plants and is reported to be a weed in more than 20 crops in 50 countries (Holm et al., 1977). It is an annual or winter annual, spreading by seed and the stems rooting at the nodes. Stems are slender, round, branching, usually prostrate and spreading with lines of fine hairs and swollen nodes at the leaf base. Leaves are in pairs on opposite sides of the stem at each node, the lower and middle leaves are stalked and the stalk often has a fringe of hairs along each edge, upper leaves are stalkless and are oval with pointed tips. Flowers are located in the axils of the leaves, about 6 mm across with five sepals and five white petals, flowering throughout the growing season and maturing seed rapidly after flowering. Seeds are reddish brown to tan colored, about 1 mm across, and covered with regular rows of small bumps. Common chickweed grows best on moist, heavy, nitrogen rich soils at optimum, constant temperature of 12–20° C. (Turkinton et al., 1980). In Canada, common chickweed can germinate throughout the growing season but has two main flushes: one is early spring while the other is in late fall.

Common chickweed belongs to the genus *Stellaria* (Table 6), subfamily Alisnoideae, family Caryophyllaceae, order Caryophyllales (Cronquist 1981). The family Caryophyllaceae consists of three subfamilies including Alsinoideae, Paronychioideae, and Silenoideae containing 13, 12, and 14 genera, respectively (Cronquist, 1981; Jalas and Suominen, 1987). The most familiar species in the subfamily Alsinoideae include the weeds such as common chickweed, mouse-eared chickweed (*Cerastium vulgatum* L.), and Knawel weed (*Scleranthus annus* L.). Subfamily Paronychioideae contains the weed Corn spurry (*Spergula arvensis* L). Subfamily Silenoideae contains a number of garden ornamentals, such as carnation (*Dianthus caryophyllus* L.) and baby's breath (*Gypsophila* sp), as well as weeds such as *Gypsophila paniculata* L., white cockle (*Lychynis alba* Mill.), cow cockle (*Saponaria vaccaria* L.), bladder Campion (*Silene cucubalis* Wibel), and night-flowering catchfly (*Silene noctiflora* L.).

TABLE 6

| Test plant species used for host-specificity screening of *Burkholderia andropogonis* against common chickweed (*Stellaria media*) based on the modified centrifugal phylogenetic and varietal strategy Caryophyllaceae |
|---|
| Caryophyllaceae |
| Subfamily Alsinoideae |
| 1. *Stellaria media* (L.) Vill. (Chickweed) |
| 2. *Scleranthus annus* L. (Knawel weed) |
| Subfamily Paronychioideae |
| 3. *Spergula arvensis* L. (Corn spurry) |
| Subfamily Silenoideae |
| 4. *Dianthus caryophyllus* L. (Carnation) |
| 5. *Gypsophila paniculata* L. (Baby's-Breath) |
| 6. *Lychynis alba* Mill. (White cockle) |
| 7. *Saponaria vaccaria* L. (Cow cockle) |
| 8. *Silene cucubalis Wibel* (Bladder Campion) |
| 9. *Silene noctora* L. (Night flowering catchfly) |
| Poaceae |
| Subfamily Festucoideae |
| Tribe Hordeae |
| 10. *Triticum aestivum* L. (Wheat, cv. Katepwa) |
| 11. *Horde = vulgare* L. (Barley, cv. Bridge) |
| 12. *Lolium perenne* (perennial ryegrass, cv. Fiesta II and Low Grow) |
| Tribe Aveneae |
| 13. *Avena sativa* L. (Oats, cv. Unknown) |
| Tribe Festuceae |
| 14. *Festuca arundinacea* Schreb. (Tall fescue, cv. Mustang II and Crossfire) |
| 15. *Festuca rubra* (Creeping red fescue, cv. Boreal and Jasper) |
| 16. *Poa pratensis* (Kentucky bluegrass, cv. Limousine and Merit) |
| Tribe Agrostideae |
| 17. *Agrostis palustris* (creeping bentgrass, cv. Penncross and Cata) |
| Subfamily Panicoideae |
| 18. *Sorghum bicolor* L. (Sorghum, cv.) |
| 19. *Sorghum sudanens* (Piper) Stapf. (Sudan grass) |
| Tribe Maydeae |
| 20. *Zea mays* L. (Corn, cv. Early Golden Bantum) |
| Fabaceae |
| Tribe Vicieae |
| 21. *Cicer arietinum* L. (Desi chick pea cv. Myles) |
| 22. *Cicer arietinum* L. (Kabuli chickpea cv. Dwelley) |
| 23. *Lens culinaris* Medic. (Lentil, cv. Laird) |
| 24. *Vicia sativa* L. (Common vetch) |
| Tribe Phasepleae |
| 25. *Pisum sativum* L. (Pea, cv. Radley) |
| Tribe Trifolieae |
| 26. *Medicago sativa* L. (Alfalfa, cv. Algonquin) |
| 27. *Trifoliem pratense* L. (Red clover) |
| 28. *Trifoliem repens* L. (White clover) |
| 29. *Trifoliem hybrid* = L. (Alsike clover) |
| 30. *Melilotus officinalis* (L.) Pall. (Sweet clover cv. Yukon) |
| Liliaceae |
| 31. *Tulip sylvestris* L. (Tulip) |

TABLE 6-continued Test plant species used for host-specificity screening of *Burkholderia andropogonis* against common chickweed (*Stellaria media*) based on the modified centrifugal phylogenetic and varietal strategy Caryophyllaceae Rubiaceae 32. *Vaccinium* sp. (Blueberry, cv.)

Linaceae

33. *Linum usitatissimum* L. (Flax, cv. Norlin)

Asteraceae

34. *Helianthus annuus* L. (Sunflower cv. S6140)
35. *Carthamus tinctorius* L. (Safflower cv. unknown)

Brassicaceae

36. *Brassica napus* L. (Argentine Canola)
  cv. Invigor 2153 (Liberty Link)
  cv. Quest (Roundup Ready)
  cv. 45A71 (Pursuit Smart)
  cv. Quantum (Conventional)
  cv. Impulse (Conventional)

TABLE 6-continued

Test plant species used for host-specificity screening of *Burkholderia andropogonis* against common chickweed (*Stellaria media*) based on the modified centrifugal phylogenetic and varietal strategy Caryophyllaceae 37. *Brassica rapa* L. (Polish Canola)
  cv. Hysyn 111
  cv. Reward The Order Caryophyllales has 11 families with major economic importance as both garden ornamentals and notable weeds (Bateman, 1985; Jalas and Suominen, 1987a; 1987b). Considering the phenogenetic relationship to common chickweed, important plants in families other than Cayophyllaceae family may include weeds, such as *Chenopodium* spp., *Amaranthus* spp., common purslane (*Portulaca oleracea* L.), and Russian thistle (*Salsola kali* L. var. *tenuifolia* Tausch), as well as vegetables, such as beet (*Beta vulgaris* L.) and spinach (*Spinacea oleracea* L.). Plants native to Canada in all families of the order Caryophyllales grow exclusively in non-cultivated areas (Scoggan, 1978). Few are common in agricultural fields, home gardens, or golf courses (Table 7).

TABLE 7

Worldwide distribution, economic importance, and Canadian native flora and their habitats in the Order Caryolphyllales[a]

| Family | Worldwide Distribution | Economic uses | Canadian native flora and their habitats |
|---|---|---|---|
| Cactaceae | Semi-desert regions of North, central and South America | Some garden and house ornamentals with local uses for fruits | Four species in two genera In dry sands, rocks, hillsides. None in cultivated lands, home gardens, golf courses |
| Aizoaceae | Pantropical, but centered in South Africa | Many greenhouse and garden ornamentals and ornamental curiosity | None |
| Phytolacceae | Tropical and subtropical, America and West Indies | Many medicinal uses, yield red dyes and are used as ornamentals and potherbs | One species In damp woods. Not in cultivated lands, home gardens, golf courses |
| Achatocarpaceae | Tropical and subtropical, America and West Indies | Woods and shrubs | None |
| Nyctaginaceae | Pantropical | *Bougainvillea* and *Mirabilis* cultivated as ornamentals; Pisonia used as vegetables | Four species in two genera In coastal sands, sandy soil, dry plains, and foothills. None in cultivated lands, home gardens, golf courses |
| Didieraceae | Dry parts of Madagascar | Rarely cultivated | None |
| Basellaceae | Tropical America | Limited use as vegetables and ornamentals | None |
| Portulacaeae | Cosmopolitan, but centered in South Africa and America | Several ornamentals and a potherb | 22 species in five genera In gravelly to heavy soils, woods, tundra, slopes, rocks, banks, lowlands. None in cultivated lands, home gardens, golf courses |

TABLE 7-continued

Worldwide distribution, economic importance, and Canadian native flora
and their habitats in the Order Caryolphyllales[a]

| Family | Worldwide Distribution | Economic uses | Canadian native flora and their habitats |
|---|---|---|---|
| Chenopodiaceae | Temperate and subtropical, particular in saline habitats | Sugar beet, beetroot, leaf beets, and spinach | 22 species in five genera In dry plains, alkaline flats, coastal sands, salt marshes, waste places, shores. None in cultivated lands, home gardens, golf |
| Amaranthaceae | Cosmopolitan, with tropical members centered in Africa | Widely cultivated as garden ornamentals and a few used as pot herbs and vegetables | Four species in the genus *Amaranthus* In alkaline moist flats, lakeshores, waste places. None in cultivated lands, home gardens, golf courses |
| Caryophyllaceae | Temperate regions, centered in the Mediterranean area | Many popular garden ornamentals, notably pinks and carnations; others are widespread weeds | 62 species in 9 general In moist meadows, montane forests, streambanks, hillsides, tundra, rocky places, damp thickets, brackish or saline shores, coastal muds and sands, salt marshes, sandy and gravelly places, barrens, cliffs, ravines, ledges, woodlands, river bars. None in cultivated lands, home gardens, golf courses |

[a]The phylogenetic relationship and other data was based on Cronqiust (1981) and Bateman (1985)

The Biocontrol Agent: *Burkholderia Andropogonis*

*Burkholderia andropogonis* (Smith 1911) Gillis et al. 1995, comb. nov. belongs to the family Burkholderiaceae, order Burkholderiales, class Betaproteobacteria, Phylum Proteobacteria (Boone et al., 2001). Several synonyms exist as *Pseudomonas andropogonis* (Smith 1911) Stapp 1928, Bacterium *andropogon* (sic) Smith 1911, *Aplanobacter stizolobii* Wolf 1920, *Pseudomonas stizolobii* (Wolf 1920) Stapp 1935 (Gillis, 1995; Viallard et al., 1998). *B. andropogonis* appears in Group A (isolated from diseased plants and nonfluorescent), Section V of *Pseudomonas* in Bergey's Manual (Palleroni, 1984). *B. andropogonis* has been reported as pathogenic to *sorghum,* corn, clover, velvet bean, and carnation. Eight other bacterial species in the same group (Group A) were reported as pathogenic to the bird's-nest fern (*Asplenium nidus*), pawpaw, cultivated mushroom, almond tree (*Prunus dulcis*), oats (*Avena sativa*), foxtail (*Chaetochloa lutescens*), *Ciccus japonica,* *Cattleya* sp., *Phalaenopsis* sp., tomato, rice, and sugarcane.

Inoculum Preparation

Stock cultures of *B. andropogonis* were stored in 15% glycerol at −80° C. For each experiment, a cryovial of stock culture was warmed to room temperature in a 36'C. water bath. A 50 gl aliquot of suspension from the vial was added to each 18×150 mm glass test tube containing 3 ml nutrient glucose broth (NGB) at a pH of 6.8. The test tubes were incubated on an orbit shaker at 200 rpm for 24 h under ambient laboratory conditions (24° C.±3). Contents of tubes were used as 'seed inoculum'. Unless otherwise stated, the bacterial culture for inoculations was produced by placing 75 ml of NGB (pH 6.8) in each 250-ml Erlenmeyer flasks, autoclaving, cooling, inoculating with 1 ml per flask of the 'seed inoculum', and incubating flasks on an orbit shaker at 200 rpm for 24 h under ambient laboratory conditions (24° C.±3). When stated, viable bacterial cell production was determined using the dilution plate count method. Serial dilutions (10×) were performed in dilution tubes containing 9 ml of sterile 0.01 M phosphate buffer, pH 7, and 100 µl of three appropriate dilutions were spread plated on nutrient glucose agar (NGA). Plates were incubated under ambient laboratory conditions for about 4 days. Colony forming units (CFU) per ml was determined by counting colonies on plates with 10–200 CFU per plate.

Plant Production

Using the modified centrifugal phylogenetic and varietal strategy (Wapshere, 1974), 36 plant species in 30 genera and 8 families were selected for the host range trial (Table 6). Test plants were grown from seed or propagated vegetatively depending on the species being tested and availability of material. Plants were planted in 10-cm diameter peat pots containing steam-pasteurized soil mix. The soil mix consisted of 140 L soil (loam, pH 6.7, 42% sand, 40% silt, and 18% clay), 107 L sand, 160 L Sunshine Growing Mix (SunGro Horticulture, Bellevue, Wash.), 62 L Fibrous Blond Shagnum Peat Moss (Premier Pro Moss, Riviere du-Loup, Quebec), 113 L vermiculite (Therm-O-Rock, Chandler, Ariz.), 230 g dolomite lime, and 150 g Super Phosphite (0-45-0) per batch of soil. Seeded pots were placed in a greenhouse with 23/20±4° C. day/night temperature, a 16 h photoperiod, an average light intensity of 300 $iEni^2s"^1$, and an average relative humidity of 45–50%. After germination, seedlings were thinned to five plants per pot.

Treatments

For each species, two sets of test plants (each set containing 15 plants) were prepared. One set was inoculated with *B. andropogonis* and the other set served as uninoculated controls. Seedlings of selected plant species at the 2- to 3-leaf stage were arbitrarily selected. For the inoculated treatment, seedlings were sprayed with the bacterial culture suspension at $10^9$–$10^{10}$ CFU/ml bacterial cells plus 0.15% Silwet L-77®, using an H-set airbrush (Paasche Airbrush Company, Harwood Heights, Ill.) at a pressure of 100 kPa. The application volume of the culture suspension was 5 ml/pot. For uninoculated control, seedlings were sprayed with 0.15% Silwet L-77®. Immediately after spraying, pots were returned to the greenhouse and placed in a randomized block design for the remainder of the experiment.

Measurements

Disease severity was visually assessed daily until the 14th day after inoculation by using the 0–11 rating scale by Horsfall and Barrett (1945). Chickweed seedlings at the 4–6 leaf growth stage were also inoculated with the same inoculum and served as a control. The experiment was conducted as a factorial experiment with species tested and inoculation levels (0 and $10^9$–$10^{10}$ CFU ml$^{-1}$) as factors. Each treatment was replicated three times.

Burkholderia andropogonis has never been reported as a pathogenic bacterium causing crop diseases in Canada (Howard et al., 1994; Martens et al., 1994). To our knowledge, this is first description of B. andropogonis as a plant pathogen in Canada (Howard et al., 1994; Martens et al., 1994). Host specificity test for 36 plant species in 30 genera and 8 families demonstrated that the CW00B006C strain of B. andropogonis is not pathogenic to the majority of major economically important crops cultivated in western Canada. Table 8 shows the plant species with disease ratings greater than 0.

TABLE 8

Disease severity results of host specificity screening for Burkholderia andropogonis

| Test plant species[a] | Disease grade[b] |
| --- | --- |
| Chickweed (Stellaria media) | 5.0 |
| Carnation (Dianthus caryophyllus) | 3.0 |
| White cockle (Lychynis alba) | 2.0 |
| Cow cockle (Saponaria vaccaria) | 4.3 |
| Baby's-Breath (Gypsophila paniculata) | 2.3 |
| Bladder Campion (Silene cucubalis) | 1.7 |
| Night-flowering catchfly (Silene noctiflora) | 3.3 |
| Sorghum (Sorghum bicolor) | NA |
| Chick pea (Cicer arietinum) | 3.0 |
| Common vetch (Vicia sativa) | 4.3 |

[a]All other species remained uninfected, severity ratings were 0.
[b]Seedlings of plants at the 2- to 3-leaf stage were inoculated with the bacterial culture suspension at $10^9$–$10^{10}$ CFU/ml bacterial cells plus 0.15% Silwet L-77 ®. The application volume of the culture suspension was 5 ml/pot. Chickweed seedlings at the 4- to 6-leavestage were also inoculated with the same inoculum and served as a control. Disease severity was visually assessed daily until the 14th day after inoculation by using the 0–11 rating scale by Horsfall and Barrett (1945).

Findings in the study demonstrated that hosts of our B. andropogonis strain isolated from common chickweed were distributed in the families Caryophyllaceae, Poaceae, and Fabaceae. No infection on clover confirmed that the bacterial isolate of the present invention possesses host specialization, supporting the conclusions reported by Moffett et al. (1996). Hosts in the Caryophyllaceae family of our B. andropogonis strain are relatively wide (Table 7). All plant species in the Silenoideae subfamily was diseased by the inoculation of B. andropogonis. In the Alsinoideae subfamily, all seedlings of common chickweed serving as positive controls were severely diseased. However, the other plant species in the same subfamily, corn spurry (Spergula arvensis), was not affected by the inoculation of B. andropogonis. In the Paronychioideae subfamily, the selected plant species, Knawel weed (Scleranthus annus) was not affected by the inoculation of B. andropogonis. Results demonstrated that this bacterium also causes disease at various levels on six other weed species common to western Canada in this family, expanding B. andropogonis' weed control spectrum as a bioherbicide.

In the Poaceae family, three plant species including corn (Zea Mays), sorghum (Sorghum bicolor), and sudan grass (Sorghum sudanens (Piper) Stapf.) were reported as hosts of B. andropogonis in the United States (Smith & Hedge, 1905; Ullstrup, 1960). Our results demonstrated that although a water-soaked lesion was observed on two of nine corn seedlings treated with B. andropogonis, disease ratings on bacterial treated corn seedlings were similar to that on untreated corn seedlings two weeks after inoculation. Three weeks after inoculation, no visible difference was observed between treated and untreated corn seedlings. Ullstrup (1960) reported that B. andropogonis caused bacterial stripe of a few very susceptible inbred corn lines and their progenies but not on commercial field corn in the United States. Our results confirmed that our selected commercial corn variety was not significantly susceptible to B. andropogonis to allow development of the typical bacterial stripe symptoms.

In the Fabaceae family, hosts of our B. andropogonis strain were restricted to Tribe Vicieae among 50 tribes (Hutchinson, 1967). Susceptible species in this Tribe include common vetch and chickpea. However, another economically important crop in this Tribe, lentil (Lens culinaris), was unaffected by this bacterium. Other major crops in this family were also unaffected by this bacterium.

Although B. andropogonis has a relatively wide plant host range, wounds plus infiltration are usually pre-requirements for the infections (Moffett et al., 1986). The absence of these prerequisites in the natural Canadian environment may explain why B. andropogonis has never been reported as a plant pathogen. Bioherbicide preparation of B. andropogonis contains a special surfactant, Silwet L-77®, that allows infiltration of bacterial cells into plant tissues without the presence of wounds (Zidack et al., 1992). Therefore, application of B. andropogonis as a bioherbicide will cause disease only on directly sprayed target weed species but not on other susceptible plant species under natural conditions. Since plants native to Canada in all families of the order Caryophyllales grow exclusively in non-cultivated areas (Scoggan, 1978) and few are common in agricultural field, home gardens, or golf courses (Table 7). Therefore, application of B. andropogonis as a bioherbicide will not cause disease on native plant species under natural conditions.

In conclusion, the use of B. andropogonis as a bioherbicide for control of common chickweed will not cause major concerns to crops and native flora in Canada.

EXAMPLE 5

Efficacy

After discovery, the key considerations in the decision to develop bioherbicides are efficacy and safety (Watson and Wymore, 1990). Weed control of the candidate agent should be assessed by the speed, amount, and ease of control. However, efficacy should not be determined by weed mortality alone. It has been reported that crop yield or economic threshold may be the most suitable index of bioherbicides because the non-complete eradication of weed populations can cause the significant increases in crop yields. In this example, the effectiveness of B. andropognis for the control of chickweed is quantified.

Efficacy under Greenhouse Conditions

Inoculum Preparation.

For all experiments, nutrient glucose broth (NGB) at a pH of 6.8 and/or chickweed extract medium (CWE) was used. To prepare chickweed extract medium, 3–5 wk old chickweed foliage was harvested from the greenhouse and stored at –20° C. until use. Using liquid nitrogen and a pestle and mortar, tissue was crushed to a powder, and combined with an equal amount of distilled water (w/v) to form thick slurry.

The slurry was filtered through 2-ply cheesecloth, filtrate was centrifuged at 18500 rcf (Eppendorf 581OR centrifuge)

for 15 minutes, supernatant was filter sterilized using a 0.22 pm bottle-top vacuum filter, and resulting sterile CWE medium was stored at 4° C. until use. Stock cultures of isolate CW00B006C were stored in 15% glycerol at −80° C. For each experiment, a cryovial of stock culture was warmed to room temperature in a 36° C. water bath. A 50 gl aliquot of suspension from the vial was added to each 18×150 mm glass test tube containing 3 ml of appropriate medium. The test tubes of were incubated on an orbit shaker at 200 rpm for 24 h under ambient laboratory conditions (24° C.±3). Contents of tubes were used as 'seed inoculum'. The bacterial culture for inoculations was produced using 75 ml of sterile NGB or CWE in 250-ml Erlenmeyer flasks inoculated with 0.5 ml per flask of the appropriate 'seed inoculum'. Unless otherwise indicated, flasks were incubated on an orbit shaker at 200 rpm for 24 h under ambient laboratory conditions (24° C.±3). When stated, viable bacterial cell production was determined using the dilution plate count method. Serial dilutions (10×) were performed in dilution tubes containing 9 ml of sterile 0.01 M phosphate buffer, pH 7, and 100 µl of three appropriate dilutions were spread plated on nutrient glucose agar (NGA). Plates were incubated under ambient laboratory conditions for about 4 days. Colony forming units (CFU) per ml was determined by counting colonies on plates with 10–200 CFU per plate.

Plant Production.

Chickweed seeds (7–10 seeds per pot) were sown in 10-cm diameter peat pots containing Sunshine Growing Mix (#1 SunGro Horticulture Canada Ltd., Seba Beach, Alberta, Canada). Seeded pots were placed in a greenhouse with 23/20±4° C. day/night temperature, a 16 h photoperiod, an average light intensity of 300 $\mu Em^{-2}s^{-1}$, and an average relative humidity of 45–50%. After germination, seedlings were thinned to five plants per pot.

Inoculation.

Unless otherwise stated, three replicate pots containing chickweed seedlings at the 4–6-leaf stage were inoculated with culture suspension using an H-set airbrush (Paasche Airbrush Company, Harwood Heights, Ill.) at a pressure of 100 kPa. Unless otherwise stated, the culture suspension consisted of $10^9$–$10^{10}$ CFU/ml bacterial. The application volume of the culture suspension was 5 ml/pot. Immediately after spraying, pots were returned to the greenhouse and placed in a randomized block design for the remainder of the experiment. Disease severity was assessed using the 0–11 rating scale by Horsfall and Barrett (1945) one, two or three wks after spraying.

Effect of Bacterial Concentration on Disease Severity.

Culture was produced using NGB as described. Culture contents of flasks were centrifuged at 2440 rcf for 10 min to form a bacterial cell pellet (Sorvall RC-5B refrigerated superspeed centrifuge). The supernatant was decanted and the bacterial cell pellet from 60 ml of culture was resuspended in 30 ml of 0.01 M, pH 7, sterile phosphate buffer amended with 0.2% Silwet L-77®. The resulting spray solution was assumed to have a concentration of $10^{10}$ cells per ml and subsequent serial dilutions of the suspension with buffer and 0.2% Silwet L-77® were made to achieve spray inoculum with cell concentrations of about $10^9$, $10^8$ $10^7$, $10^6$ and $10^5$ cells per ml. The viable bacterial concentration of each spray solution was then determined. The actual viable bacterial concentrations of each spray solution were very close to desired concentrations at $0.98 \times 10^{10}$, $1.8 \times 10^9$, $1.0 \times 10^8$, $1.8 \times 10^7$, $1.6 \times 10^6$, and $1.6 \times 10^5$ CFU/ml. Chickweed seedlings were inoculated with each spray solution. Control plants were inoculated with sterile 0.01 M phosphate buffer plus 0.2% Silwet L-77®. Efficacy of each solution was determined as described.

Effect of Spray Solution pH on Disease Severity.

Bacterial inoculum was produced using NGB as described. Culture contents of each flask were centrifuged at 2440 rcf for 10 min to form a bacterial cell pellet (Eppendorf 5810R centrifuge). Supernatant was decanted and the bacterial cell pellet from 40 ml of culture was resuspended in 20 ml of 0.1 M sterile phosphate buffer containing 0.2% Silwet L-77® with pHs from 6 to 8 at increments of 0.2. Chickweed seedlings were inoculated with each spray solution having different pH. Control plants were inoculated with sterile 0.1 M phosphate buffer of the appropriate pH plus 0.2% Silwet L-77®. Efficacy of each solution was determined as described.

Effect of Surfactant Type and Concentration on Disease Severity.

Inoculum was produced using NGB as described. Five organosilicone-based surfactants (Loveland Industries, Inc., Greeley, Colo.) were selected including Silwet L-77® (silicone-polyether copolymer 100%), Freeway (silicone-polyether copolymer and alcohol ethoxylates 100%), Phase (methylated esters of fatty acids and organosilicone surfactant fluids 100%), Tactic (synthetic latex plus organosilicone surfactant 62.5% and inerts 37.5%), and motion (polymethylsiloxane-copolymer and non-ionic surfactant 100%). Concentrations of 0.1, 0.2, and 0.3% were included for Silwet L-77® and Intac while surfactant concentrations of 0.1, 0.2, 0.3, and 0.5% were included for remaining three surfactants. Surfactants were added to bacterial inoculum just prior to spraying. Efficacy of different surfactants was determined as described with a treatment consisting of NGB and surfactant serving as a control for each bacterial treatment.

Effect of Repeat Application on Disease Severity.

Inoculum was produced using NGB as described. Replicate pots containing chickweed seedlings at the 4–6-leaf stage were initially inoculated with bacterial solution produced as described and amended with 0.2% Silwet L-77® just prior to spraying. Immediately after spraying, pots were returned to the greenhouse and placed in a randomized block design. Inoculated common chickweed seedlings were then resprayed with bacterial inoculum, produced as described and amended with 0.2% Silwet L-77 just prior to spraying, 2, 6, and 9 days after initial application. One replicate set of pots with no repeat spray application was maintained. Control treatments with NGB and surfactant were included for all bacterial treatments. Disease severity was assessed beginning 1 wk after the initial bacterial application.

Effect of Bacterial Growth Medium and Inoculum Growth Stage on Efficacy.

Inoculum was produced using both CWE and NGB as described with incubation of bacterial inoculum in each medium for 24, 48 or 72 hours. Inoculation of flasks was staggered at 24 h intervals such that all inoculum was ready at the same time. Viable bacterial cell concentration of each treatment was determined as described prior to amendment with 0.15% Silwet L-77® for spray application. Control treatments consisting of sterile medium and wetting agent were included for both NGB and CWE. Disease severity was assessed as described.

Effect of Bacterial Growth Stage and Chickweed Growth Stage on Disease Severity.

Inoculum was produced using CWE as described. Two trials to study the impact of chickweed growth stage on disease severity were conducted. For trial 1, flasks of bacterial inoculum were incubated 24 hours as described. For trial 2, flasks of bacterial inoculum were incubated either 24 or 48 hrs prior to determination of viable bacterial cell concentration as described and amendment with 0.15% Silwet L-77® for spraying. Replicate pots of chickweed seeded and grown under greenhouse conditions as described for one (cotyledon growth stage), two (2–4 leaf stage), three (6–8 leaf stage) or four weeks were inoculated with bacterial or control solution. Spray solution for control treatments consisted of tap water and 0.15% Silwet L-77 for trial 1 and uninoculated CWE and 0.15% Silwet L-77 for trial 2. Disease severity for both trials was assessed as described.

Infectivity and Disease Severity on Group 2 Herbicide Resistant Chickweed.

Inoculum was produced using NGB as described. Group 2 herbicide resistant chickweed seeds were obtained from the ARC Weeds Research Laboratory. Previous tests indicate that the average survival rate of the herbicide resistant seed set with 1× and 2× Ally (metsulfuron methyl) application was 73.5 and 35.2%, respectively (O'Donovan, et al., 1994). The chickweed seed set used for all other experiments was included as a herbicide susceptible positive control. Both herbicide resistant and susceptible seedlings were produced as described and seedlings of both seed sets at the 6–8 leaf stage were inoculated with the bacterial inoculum using the previously described method. Differences in infectivity and disease severity between the herbicide resistant and the herbicide susceptible populations were compared as described.

Efficacy under Field Conditions

Experiments Conducted in Outside Pots.

Efficacy of *B. andropogonis* for the control of chickweed under natural conditions was first evaluated in large pots set outside. Two experiments were conducted, one in 2001 (July 24–September 14) and the second in 2002 (May 30–July 31). Results from the two experiments were not pooled because the variances were not homogeneous according to Bartlett's test (Gomez & Gomez, 1984). However, a similar trend was observed and the results from 2001 are presented.

For both experiments, chickweed plants were produced in 53-cm-diameter fiber pots filled with soil collected from a field at the ARC, Vegreville experimental site (loam, pH 6.7, 42% sand, 40% silt, and 18% clay) and placed outside on the ground where building walls would provide some shade. Chickweed seeds were sown in the pots 3–4 weeks prior to spraying by sprinkling seeds evenly over the soil surface, then lightly sprinkling soil over the seeds. Pots were watered as necessary using an outside tap throughout the experiment. Bacterial inoculum was prepared as described using NGB and 24 h incubation of flasks for experiment 1 and CWE and 48 h of incubation for experiment 2. Inoculum at a cell concentration of $3.0 \times 10^9$ CFU/ml for experiment 1 and $5.0 \times 10^9$ CFU/ml for experiment 2, with a surfactant concentration of 0.15% Silwet L-778 for both experiments was used. A control treatment with NGB and wetting agent was included for experiment 1, while a control with tap water and wetting agent was included for experiment 2. Chickweed plants were sprayed at approximately the 6-leaf stage. For experiment 1, pots with chickweed seedlings at the 6-leaf stage were brought inside and placed, 3 replicate pots at a time, in the spray chamber. Each pot was sprayed with 100 ml of appropriate solution using an airbrush at 100 kPa. After spraying, pots were immediately placed back outside. For experiment 2, a 2L Spray-Doc compressed air sprayer (Gilmour Manufacturing Co., Somerset, Pa., USA) was used to spray about 115 ml per pot without moving them from their outside location. Plants were assessed for symptoms using the 0–11 rating scale by Horsfall and Barrett (1945) when they became most apparent, about 2 weeks after spraying. Daily weather conditions during the experiments were recorded including maximum and minimum temperatures (° C.), precipitation (mm), sunlight period (h); and average radiation (watts/m$^2$). Dry weight per pot was determined 4 weeks after spraying by cutting aerial parts at the soil level, drying in a paper bag for 48 h at 70° C., and weighing. The dry weight (DW) data were expressed as percent reduction in biomass compared with biomass of controls and calculated using the formula: Dry weight reduction (%)=(DW in control−DW in inoculated treatment)/DW in control×100. The experiments were arranged in a completely randomized design. Data was analyzed by SAS ANOVA.

Experiments Conducted in Field Plots.

Efficacy of CW00B006C for the control of chickweed at different growth stages under natural conditions was further evaluated in field plots. Two field trials were conducted at the ARC Vegreville experimental site in 2002: trial one was conducted from May 27–July 29 and trial 2 from June 24–August 30. Results from the two trials were not pooled because the variances were not homogeneous according to Bartlett's test (Gomez & Gomez, 1984). However, a similar trend was observed between trials and the results from trial 1 are presented.

Figure 14:
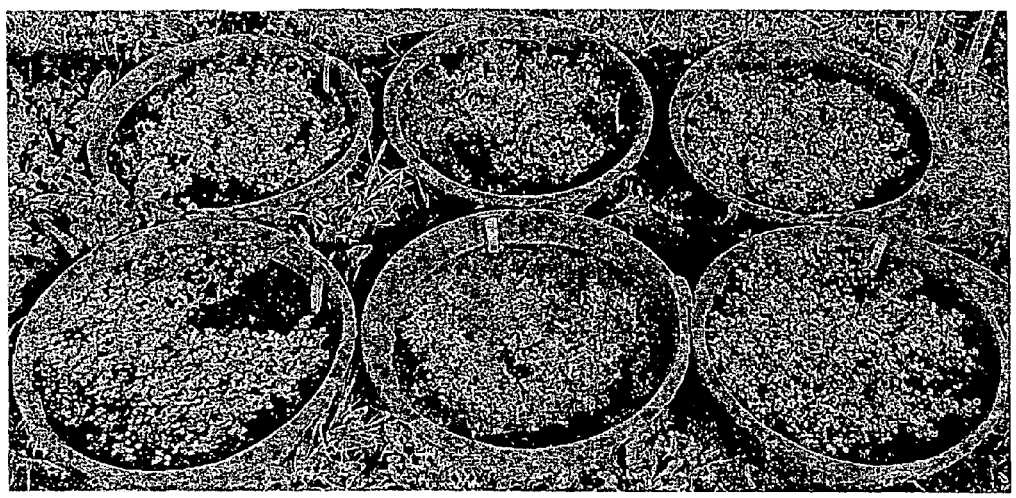
FIG. 14 shows the infectivity of *Burkholderia andropogonis* on chickweed under field conditions (Left—Treated, Right—Control).

A mini-plot (0.5 m×1.0 m) design with a 0.5 m boarder of bare earth surrounding each split plot was used (FIG. 14). The main experimental factor was chickweed growth stage, with seeding dates at 1 wk intervals (Jun. 17, Jun. 24, Jul. 2, and Jul. 8, 2002 for trial 1), while the subplot factor was bacterial application rate (0 or $10^9$ CFU/ml). For each of four replicate 0.5 m×1.0 m plots one half (0.5 m×0.5 m) was sprayed with control solution and the other half with bacterial inoculum. For each seeding date, 2 g of chickweed seed were evenly sown over the surface of a 0.5 m×1 m plot and lightly covered with soil until seeds were no longer visible (about 2 mm deep). Unless soil was wet at the surface from recent rains, all plots were watered using a watering can with a sprinkler nozzle. The soil surface was kept moist at all times until seeds germinate. Weeds other than chickweed in the boarder areas of plots were hand-removed. Bacterial inoculum was produced using CWE with 48 h incubation in flasks as described. When the youngest chickweed seedlings reached the cotyledon growth stage, bacterial inoculum or tap water (control) plus 0.15% Silwet L-77® was sprayed on each subplot at an application volume of 150 ml per 0.5 m×0.5 m subplot using a 2L Spray-Doc compressed air sprayer (Gilmour Manufacturing Co., Somerset, Pa., USA). Efficacy was assessed beginning 1 wk after spraying as described. Twenty-eight (28) days after treatment, the aboveground dry biomass of chickweed was determined. All percentage data were arc sine-transformed before analysis (Gomez & Gomez, 1984). Experiments were analyzed with an analysis of variance considering the effect of main and subplot factors and their interaction, using PROC ANOVA procedure in SAS (SAS Institute Inc., 1990). Treatment means were separated using LSD at the 5% level of significance.

Efficacy under Greenhouse Conditions

Effect of Bacterial Concentration on Disease Severity.

Figure 6:
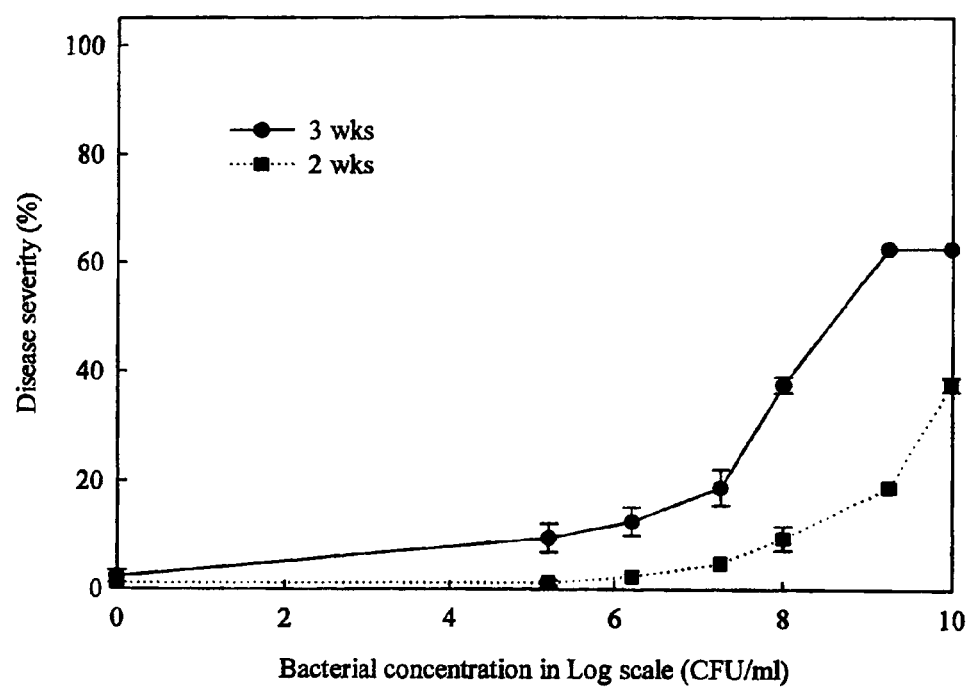
FIG. 6 shows the effect of CW00B006C bacterial concentration on the disease severity of chickweed.

Disease was observed on chickweed seedlings with all bacterial concentration treatments two weeks after spraying. Disease severity significantly increased when the bacterial concentration was increased (FIG. 6). Disease severity was also significantly greater 3 weeks versus 2 wks after spraying. About 65% disease severity was observed with the bacterial concentration of $10^9$ and 1010 CFU/ml three weeks after spray.

Effect of Spray Solution pH.

No damage was observed on control plants. Spray solution pH did not affect weed control efficacy in the pH range of 6–8.

Effect of Surfactant Type and Concentration on Disease Severity.

Figure 7:
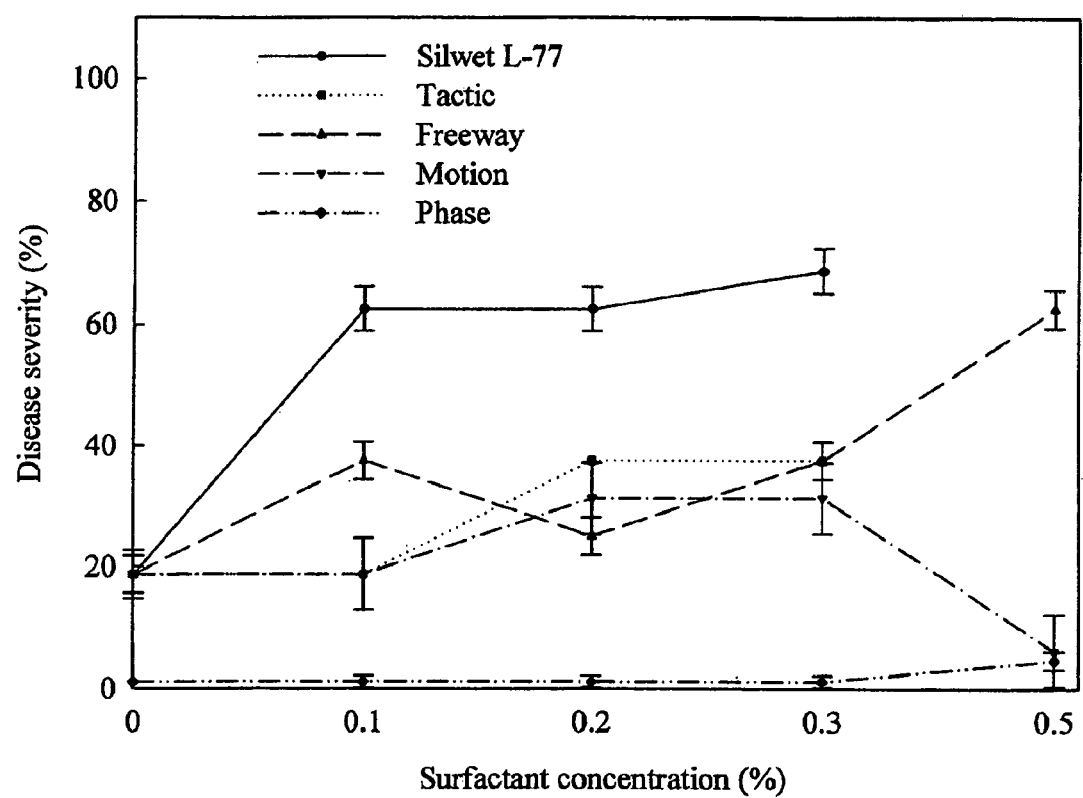
FIG. 7 shows the effect of surfactant type and concentration on disease severity of chickweed caused by *Burkholderia andropogonis*.

Effectiveness of chickweed control with *B. andropogonis* was affected by surfactant type (P>0.001), concentration (P>0.003), and their interaction (P>0.001). Of the five surfactants studied, Silwet L-77® significantly enhanced the bacterial efficacy for the control of chickweed while the remaining surfactants did not show any efficacy enhancement (FIG. 7). There was no significant difference in efficacy among treatments of 0.1%, 0.2%, and 0.3% Silwet L-77®. However, higher concentration of Silwet L-77® in control treatments showed higher phytotoxicity to chickweed seedlings. Findings in this study suggest that the best concentration of Silwet L-77® to be used with the bacterial inoculum is between 0.1% and 0.2%.

Effect of Repeat Application on Disease Severity.

Figure 8:
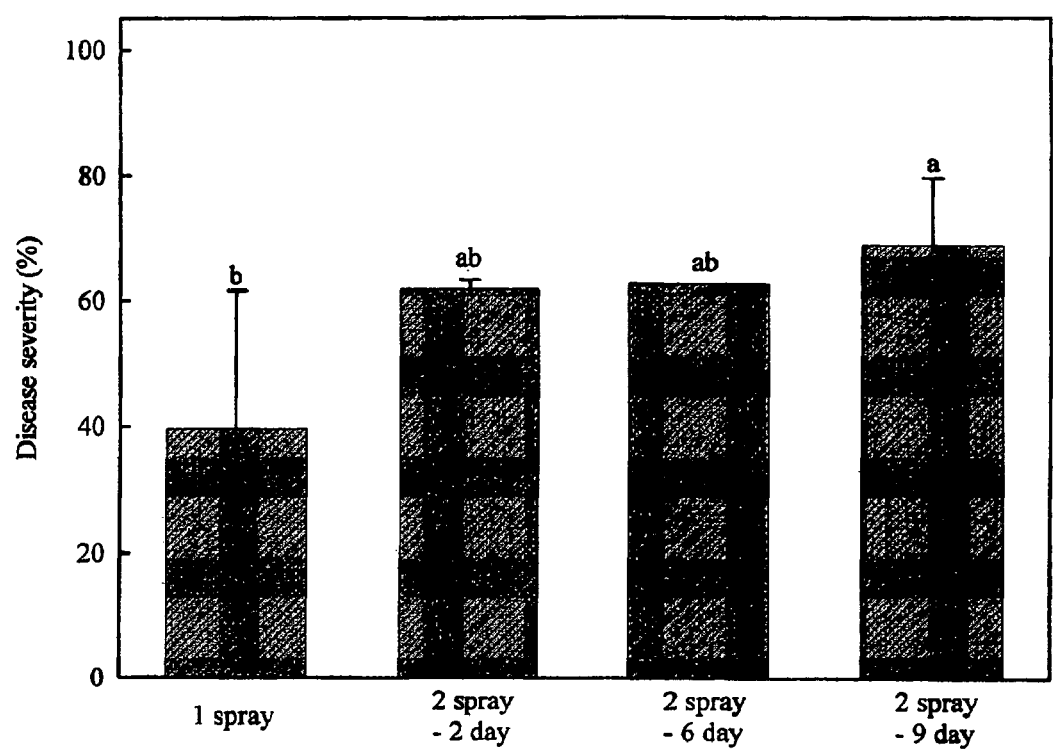
FIG. 8 shows the effect of repeat application on disease severity of chickweed caused by *Burkholderia andropogonis*.

Repeat application of the bacterial inoculum enhanced disease severity on chickweed seedlings caused by *B. andropogonis*, but this enhancement varied with the time interval of the second application (FIG. 8). Significant enhancement of disease severity on chickweed was observed with the repeat application nine days after the first application. Therefore, repeat application could be a method to improve the efficacy of *B. andropogonis* as a bioherbicide against chickweed. Effect of application frequency and time interval should be further investigated.

Effect of Bacterial Growth Medium and Inoculum Growth Stage on Disease Severity.

Figure 9:
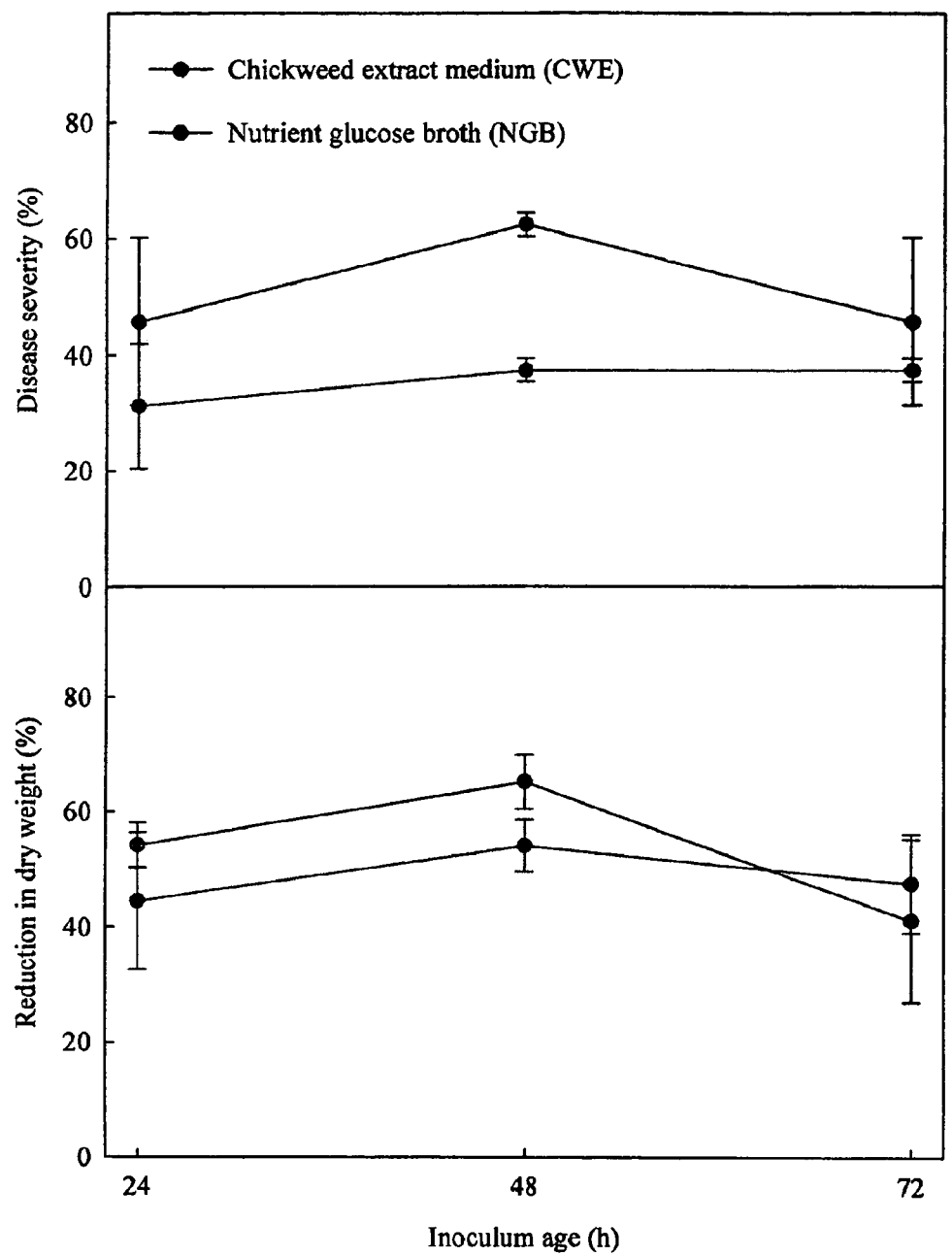
FIG. 9 shows the effect of bacterial growth medium and inoculum growth stage on disease severity of chickweed caused by *Burkholderia andropogonis*.

Disease severity was significantly affected by the addition of chickweed extract to the culture medium (P>0.0071) and the inoculum growth stage (P>0.0176) (FIG. 9). Similar patterns were observed for the percent dry weight reduction (P>0.036 for the addition of chickweed extract and P>0.048 for the inoculum growth stage). Inoculum growth stage at 48 h resulted in the greatest disease severity and percent dry weight reduction. Both disease severity and percent dry weight reduction caused by the bacterium cultured in CWE medium for 48 h were significantly greater than that caused by the bacterium cultured in NGB.

Effect of Inoculum Growth Stage and Chickweed Growth Stage on Disease Severity.

Figure 10:
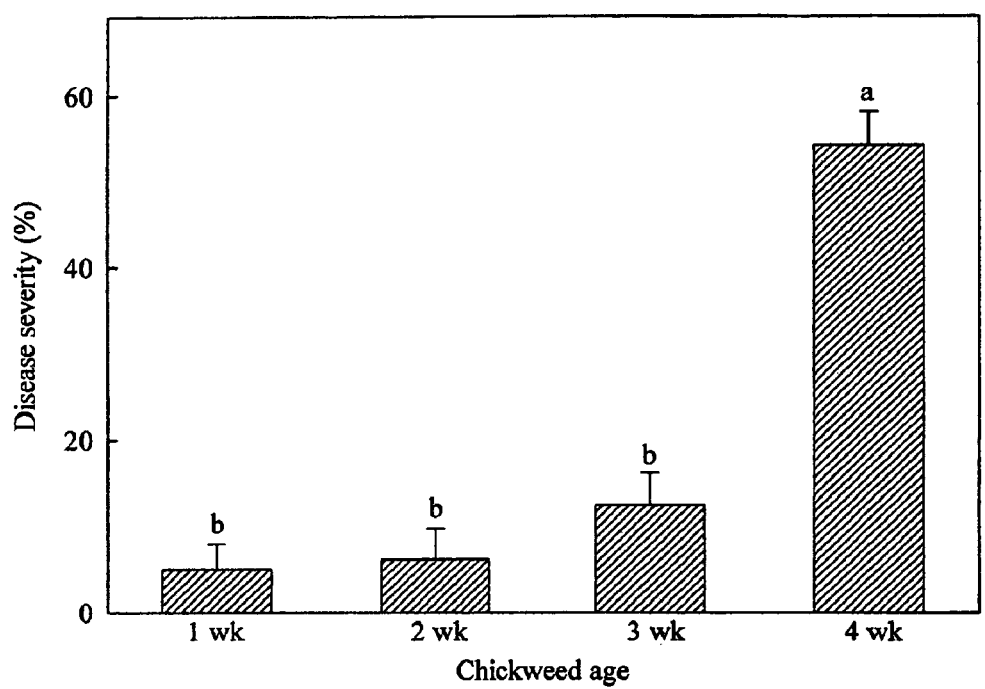
FIG. 10 shows the effect of chickweed growth stage on disease severity of chickweed caused by *Burkholderia andropogonis*.

Chickweed seedlings at different growth stages responded differently to the fungus *B. andropogonis*. Disease severity was increasing with older chickweed growth stage (FIG. 10). The highest disease severity was observed with the 4-wk-old chickweed seedlings. Disease severity in 4-wk-old chickweed seedling caused by *B. andropogonis* was significantly greater than that in 1-, 2-, or 3-wk-old chickweed seedlings (FIG. 10). However, there was no difference in percent dry weight reduction among chickweed seedlings at different growth stages treated with *B. andropogonis*.

Figure 11:
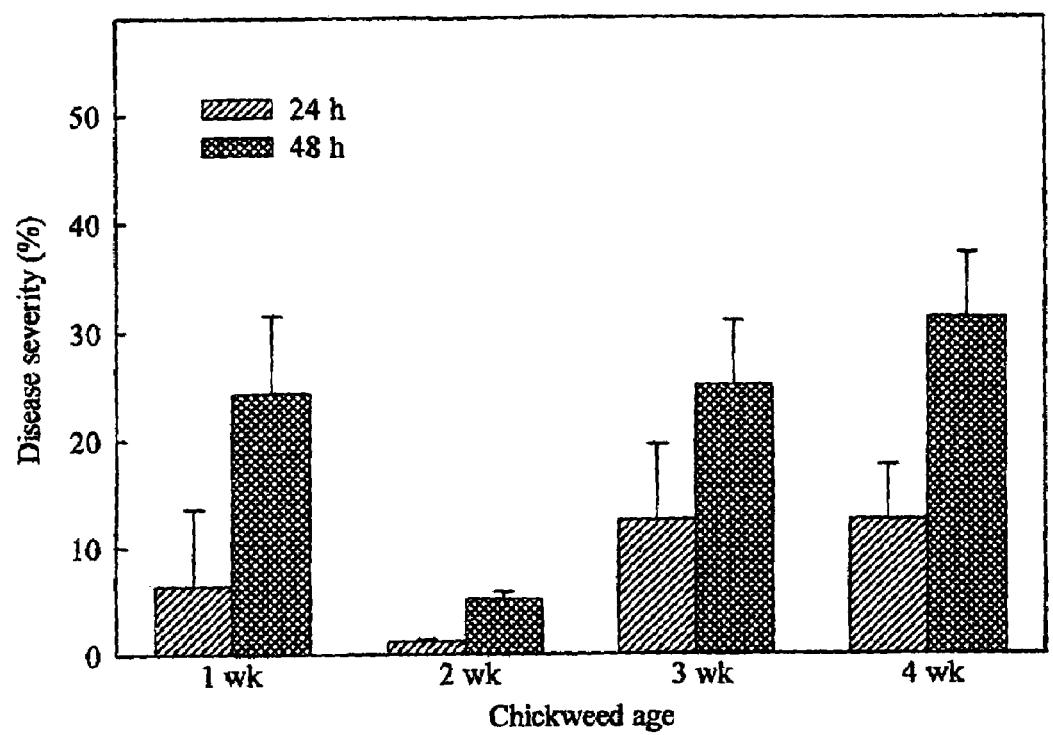
FIG. 11 shows the effect of bacterial growth stage and chickweed growth stage on disease severity of chickweed caused by *Burkholderia andropogonis*.

Inoculum growth stage significantly affected disease severity in chickweed seedlings caused by *B. andropogonis* (FIG. 11). Inoculum cultured for 48 h caused greater disease severity in chickweed seedlings at all four growth stages than inoculum cultured for 24 h. For both inoculum growth stages, disease severity was increasing with older chickweed growth stage. However, there was no difference in percent dry weight reduction of chickweed seedlings at each of four growth stages treated with inoculum cultured for 24 h or 48 h. Statistically, no interaction between inoculum growth stage and chickweed growth stage was observed (P>0.7218). Therefore, inoculum growth stage at 48 h and chickweed growth stage at 4 wk (6–8 leaf) are optimal for *B. andropogonis* to cause disease in chickweed.

Infectivity and Disease Severity on Group 2 Herbicide Resistant Chickweed.

Herbicide resistant seedlings were also susceptible to the bacterial treatment. There was no difference in disease severity between the herbicide resistant and the herbicide susceptible seedlings when treated with the same bacterial inoculum. Therefore, the use of *B. andropogonis* provides a new approach to combat Group 2 herbicide resistance in chickweed and may mitigate the development of herbicide resistance.

Efficacy under Field Conditions.

Experiments Conducted in Outside Pots.

Figure 12:
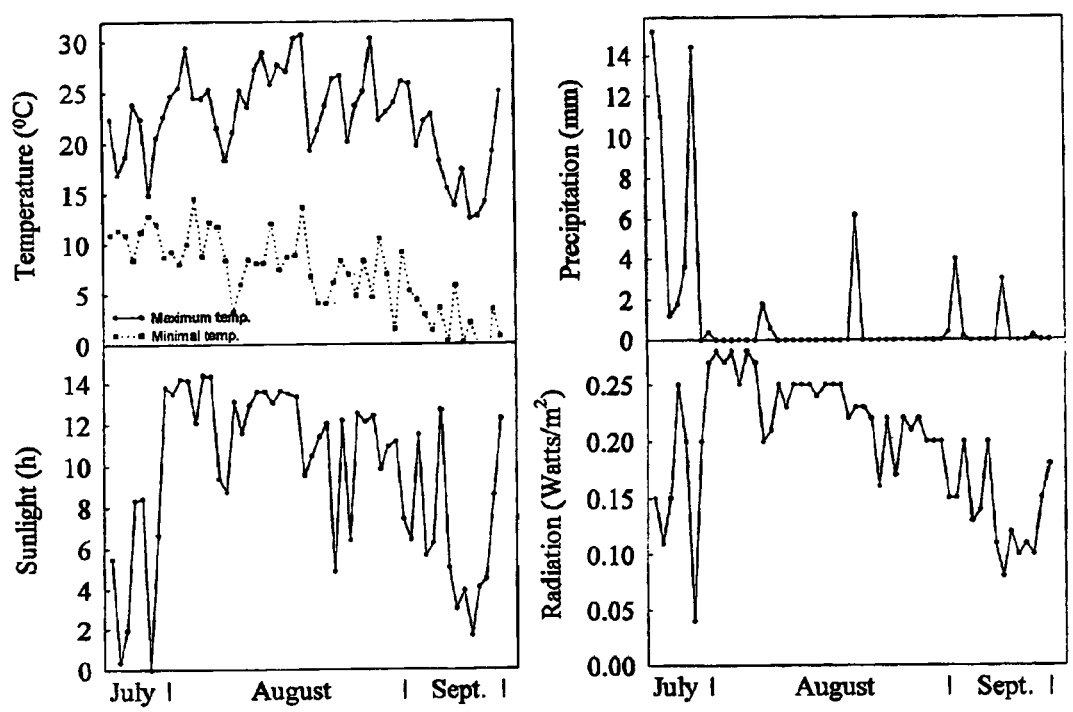
FIG. 12 shows the daily weather conditions from Jul. 24 to Sep. 14, 2001 recorded during the field evaluation of chickweed control with bacterial strain CW00B006C. (A) Maximum and minimum temperatures (° C.), (B) Precipitation (mm), (C) Sunlight period (h), and (D) Average radiation (watts/$m^2$).
Figure 13:
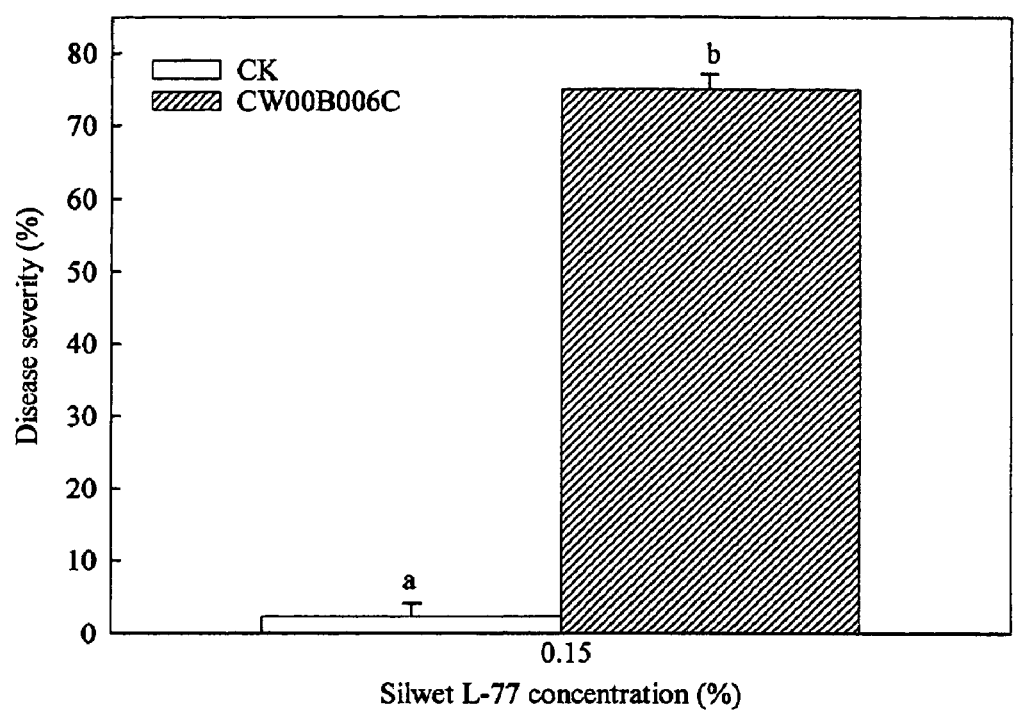
FIG. 13 shows the disease severity on chickweed grown in outside pots caused by *Burkholderia andropogonis*.

Severe disease was observed on chickweed seedlings 1 wk after bacterial treatment. Two wks after inoculation, disease severity was rated as 75% (FIG. 13). Seventy two percent dry weight reduction was obtained 4 weeks after inoculation. Disease incidence reached 100% (FIG. 14). Maximum and minimum temperatures (° C.), precipitation (mm), sunlight period (h), and average radiation (watts/m$^2$) during this experiment are shown in FIG. 12.

Experiments Conducted in Field Plots.

Figure 15:
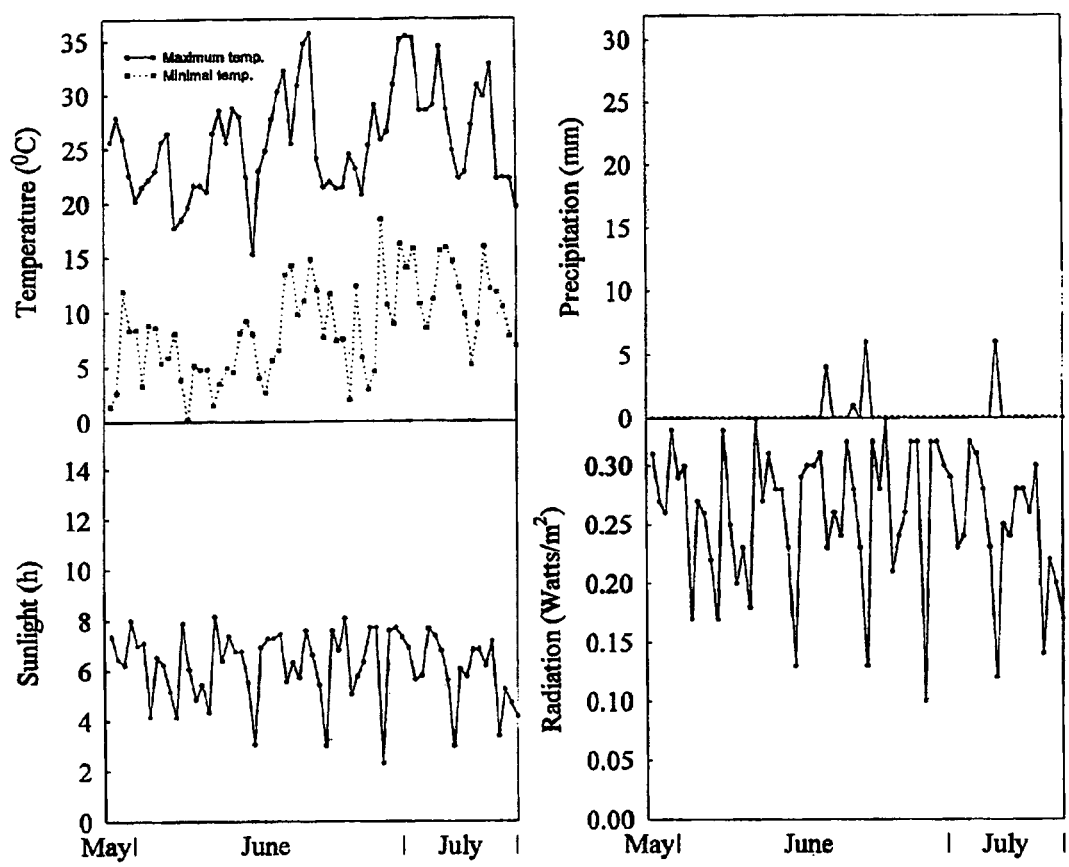
FIG. 15 shows the daily weather conditions from May 27 to Jul. 29, 2002 recorded during the field evaluation of chickweed control with bacterial strain CW00B006C. (A) Maximum and minimum temperatures (° C.), (B) Precipitation (mm), (C) Sunlight period (h), and (D) Average radiation (watts/$m^2$).
Figure 16:
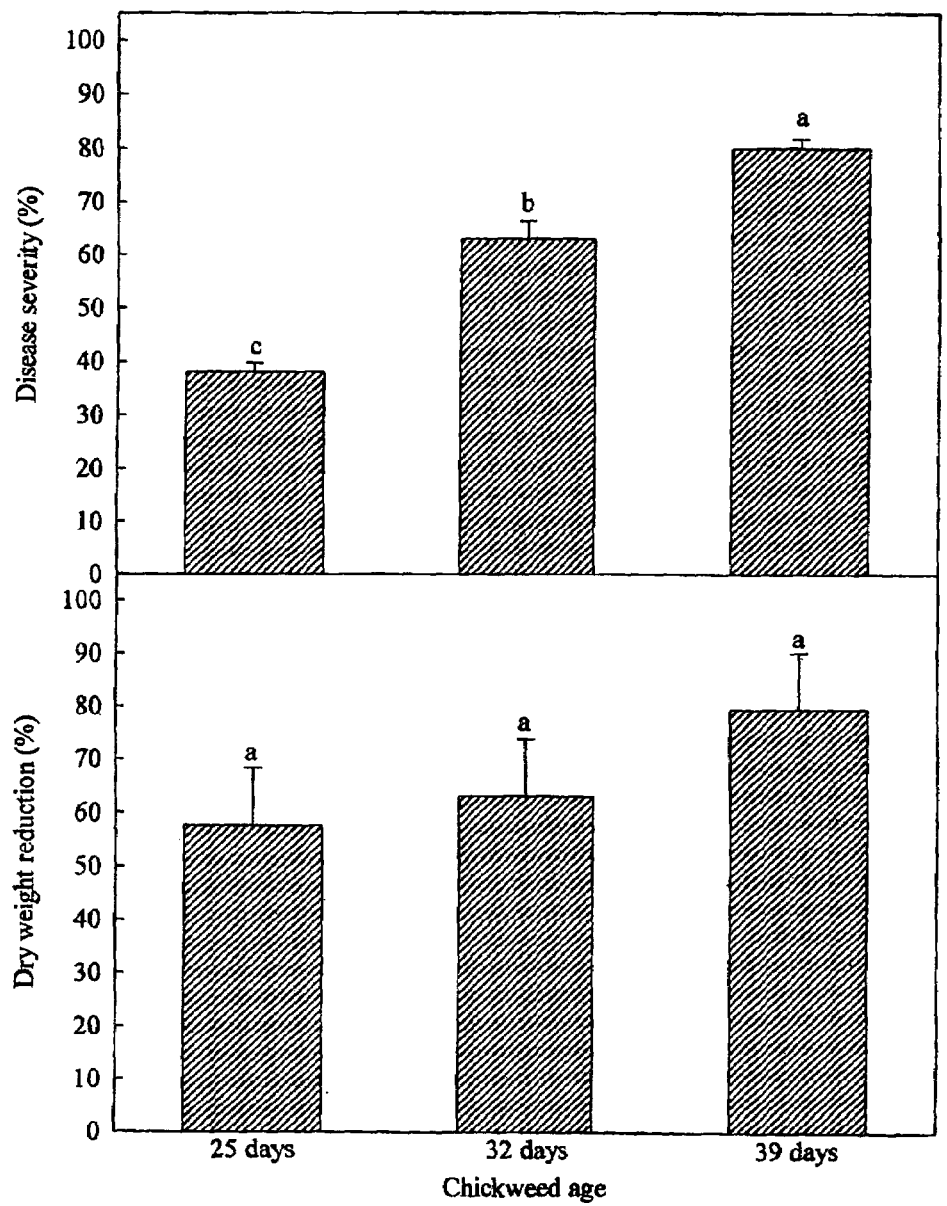
FIG. 16 shows the disease severity and dry weight reduction of chickweed caused by *Burkholderia andropogonis*.
Figure 17:
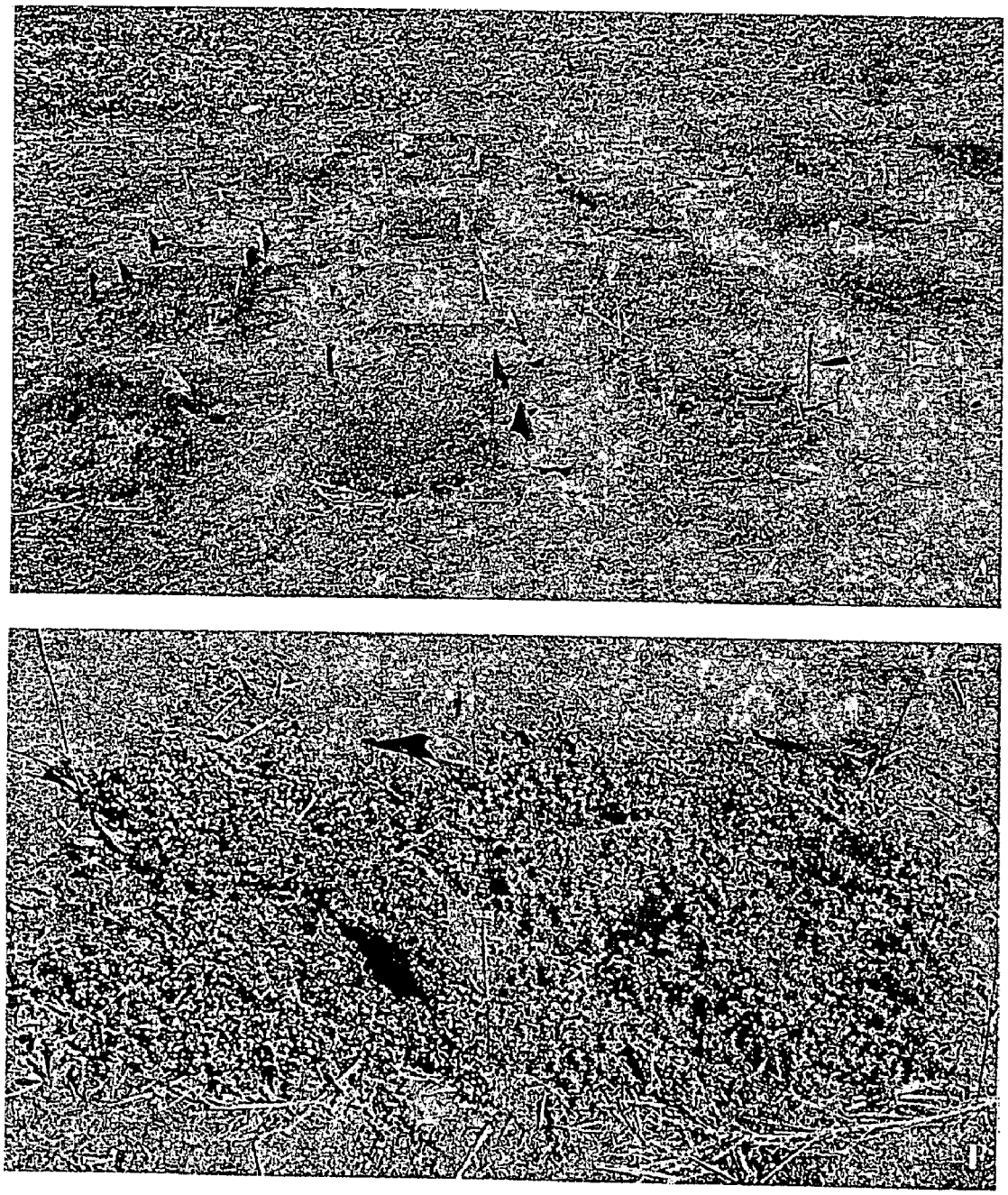
FIG. 17 shows chickweed control with the bacterium *Burkholderia andropogonis* (A) Field trial conducted in 2002 and (B) Detailed weed control performance in one plot.

Severe disease was observed on chickweed seedlings 1 wk after bacterial treatment. Disease incidence reached 100% (FIG. 17). Chickweed seedling at different growth stages exhibited different disease severity (FIG. 16). The greatest disease severity was observed on the oldest chickweed seedlings (about 80%), the least disease severity on the youngest chickweed seedlings (about 38%). However, there was no significant difference in dry weight reduction, ranging from 57.6% to 79.5%, among the different growth stage treatments (FIG. 16). Maximum and minimum temperatures (° C.), precipitation (mm), sunlight period (h), and average radiation (watts/m$^2$) during this experiment are shown in FIG. 15. Higher temperature and less precipitation might contribute to greater efficacy of *B. andropogonis* for control of chickweed. If this was true, this bacterium possesses excellent potential as a bioherbicide in western Canada due to the common dry conditions.

Production of two amino acids, 'rhizobitoxine and hydroxyreonine, has been considered as a general feature of *Burkholderia andropogonis* (Mitchell and Frey, 1988). However, potential for the use of these two amino acids to control weeds have not been extensively evaluated. Recently, several studies have demonstrated that amino acids and/or peptides can be used as biologically based herbicides (Duke et al., 2002). For example, five dipeptides from corn gluten hydrolysate can control both grasses and broadleaf weeds, with alanylalanine being the most active (Liu and Christians, 1994). In the following example it was determined whether the natural products produced by *Burkholderia andropogonis* have any herbicidal activity against chickweed.

EXAMPLE 7

Activity of Fermentation Broth of *Burkholderia andropogonis* in Chickweed Control Materials and Methods A cryovial of stock culture was warmed to room temperature in a 36° C. water bath. Streak plates were then made on King's medium B agar Petri plates (KB; 20 g proteose peptone #3 (Difco), 1.5 g. $K_2HPO_4$, 1.5 g $MgSO_4 \cdot 7H_2O$, 15 ml glycerol, 15 g Bacto Agar (Difco), 1 L distilled water) using the stock culture. After 24 h incubation under ambient laboratory conditions on KB agar, a loopfull of cells was transferred to each 18×150 mm glass test tube containing 3 ml yeast-glucose broth (YGB; 5 g yeast extract (Difco), 5 g glucose, 0.3 g $MgSO_4$, 3.9 g $K_2HPO_4$, 3.8 g $KH_2PO_4$, 1 L distilled water) at a pH of 6.8. The test tubes were incubated on an orbit shaker at 200 rpm for 24 h under ambient laboratory conditions (24° C.±3). Contents of tubes were combined as 'seed inoculum' and 0.5 ml of the 'seed inoculum' was used to inoculate each 500 ml flask containing 150 ml of filter sterilized, pH 6.8, Hoitink & Sinden chemically defined medium (HS; 10 g glucose, 3.6 g $K_2HPO_4$, 4.1 $KH_2PO_4$, 0.2 g $MgSO_4$, 1 g $NH_4Cl$, 1 mg biotin, 1 L distilled water). Flasks were incubated on an orbit shaker at 200 rpm for 6 d under ambient laboratory conditions (24° C.±3). Contents of flasks were combined and viable bacterial cell production was determined using the dilution plate count method as previously described. Culture was centrifuged 10 minutes at 2440 rcf (Eppendorf 5810R centrifuge), supernatant was poured from each tube and passed through a 0.22 gm bottle-top vacuum filter to remove all bacterial cells.

Heat Stability of the Cell-Free Culture Filtrates

A sample of cell-free filtrate was autoclaved 30 minutes at 121° C. to determine the effect of heat on the bacterial phytotoxins.

Effect of the Cell-Free Culture Filtrates on Chickweed Root Growth

A sample of both the autoclaved and unautoclaved cell-free filtrate was used for a laboratory assay designed to study the effects of the bacterial phytotoxins on chickweed seed germination and seedling root growth. A Whatman #1 filter paper was placed in replicate glass Petri Plates. Solutions of autoclaved and unautoclaved cell-free filtrates at 100, 50, 25, 12.5 and 6.25% of the initial concentration were prepared using sterile distilled water. A control of sterile, distilled water was also prepared. A 5 ml aliquot of the appropriate treatment was pipetted into each of three replicate Petri plates. Using forceps, four chickweed seeds, as used for all other experiments, were placed in each plate. Plates were placed on the laboratory bench under ambient laboratory conditions (21±2° C.) for incubation and arranged in a randomized block design. Seed germination, seedling root length (mm), and seedling appearance were assessed after 1 wk.

Diseases Caused by the Cell-Free Culture Filtrates

Figure 18:
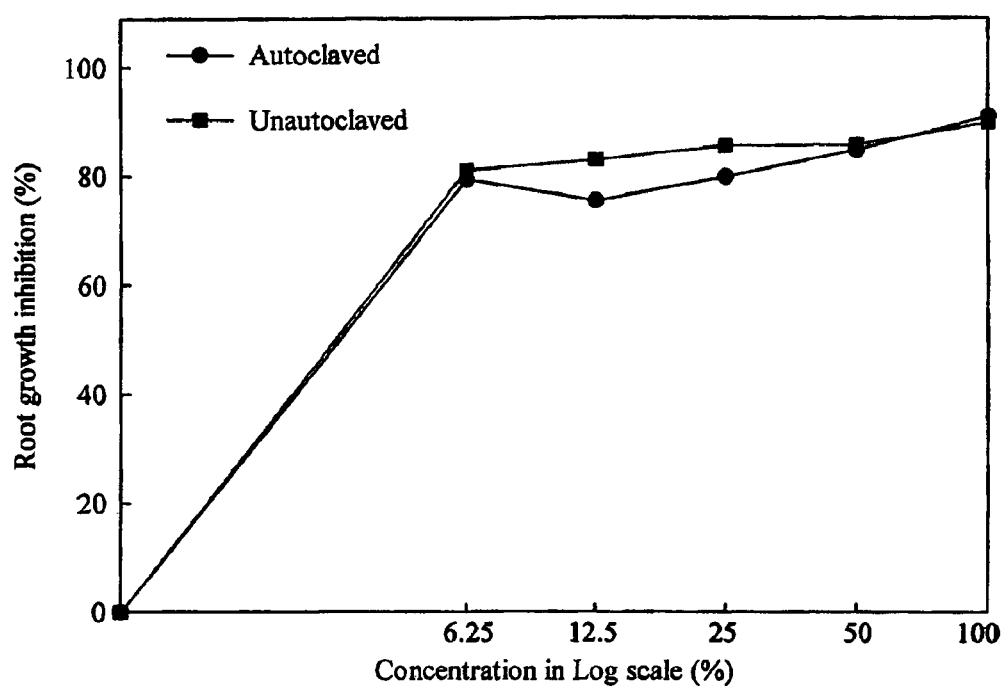
FIG. 18 shows the effect of cell free culture filtrates of CW00B006C on root growth of chickweed seedlings.

Remaining autoclaved and unautoclaved cell-free filtrate was then shell frozen in Fast-Freeze Flasks (Labconco), freeze-dried, and used to inoculate chickweed seedlings in the greenhouse. Once dry, samples were stored at −80° C. until use. Freeze-dried samples were resuspended in distilled water at a concentration of 10 times that of the original by gentle shaking. For the concentrated, unautoclaved cell-free filtrate, one 15 ml sample was amended to contain 0.1% Silwet L-77®, a second to contain 0.2% Silwet L-77®, a third was amended to contain 0.5% Tween 80 as a wetting agent and a fourth sample was left unamended. The autoclaved sample was amended to contain 0.2% Silwet L-77®. Control treatments with freeze-dried HS medium and wetting agent were also prepared. Three replicate pots containing chickweed seedlings at the 6–8-leaf stage were inoculated for each treatment using an H-set airbrush (Paasche Airbrush Company, Harwood Heights, Ill.) at a pressure of 100 kPa. Plants were grown as previously described. Immediately after spraying, pots were returned to the greenhouse and placed in a randomized block design for the remainder of the experiment. Plants were monitored for any symptoms for 3 wks following spraying Cell free culture filtrates from HS medium did not affect chickweed seed germination. However, they caused completely chlorotic chickweed seedlings and significantly inhibited root growth (FIG. 18). The activity of root growth inhibition and chlorosis from the cell-free culture filtrates was not affected by heat, i.e. autoclave vs. unautoclave, suggesting the natural products produced by CW00B006C are heat stable.

In the greenhouse studies, approximately 4–6 days after spraying, slight to moderate chlorosis was visible on new leaves of chickweed sprayed with all autoclaved and unautoclaved cell-free filtrates amended with Tween-80 and Silwet L-77®. There was no difference in disease severity on chickweed seedlings between heat treatments, confirming the natural products produced by CW00B006C was heat stable. New leaves on plants showing symptoms were pale yellow or white. No symptoms were seen on chickweed sprayed with cell-free filtrate without wetting agent or on control treatments. Thus, bacterial natural products can be used as a biologically based herbicide for the control of chickweed.

All citations are herein incorporated by reference.

The present invention has been described with regard to preferred embodiments. However, it will be obvious to persons skilled in the art that a number of variations and modifications can be made without departing from the scope of the invention described herein

LITERATURE CITED

1. Allen, R. N., A. C. Hayward, W. J. Halliday and J. Fulcher. 1970. Bacterial blight of *Vicia sativa*: aetiology of disease and identification of the pathogen. Australian Journal of Biological Science 23:597–606.
2. Bagsic-Opulencia, R. D., A. C. Hayward and M. Fegan. 2001. Use of ribotyping and random amplified polymorphic DNA to differentiate isolates of *Burkholderia andropogonis*. J. Appl. Microbiol. 91: 686–696.
3. Bateman, G. 1985. Flowering Plants of the World. Croom Helm Publishers Ltd, Beckenham, Kent, UK. pp. 63–76.
4. Boyette, C. D., Quimby, P. C. Jr., Connick, W. J., Daigle, D. J. and Fulgham, F. E. 1991. Progress in the production, formulation, and application of mycoherbicich. Pages 209–222 in TeBeest, D. O. (ed) Microbial Control of Weeds. Chapman & Hall, New York.
5. Burkholder, W. H. 1957. A bacterial disease of clover and velvet beans. Phytopathology 47:48–50.
6. Caruso, F. L. 1984. Bacterial blight of chickpea incited by *Pseudomonas andropogonis*. Plant Disease 68:910–913.

7. Charudattan, R. 2001. Biological control of weeds by means of plant pathogens: significance for integrated weed management in modern agro-ecology. Biocontrol 46:229–260.
8. Churchill, B. W. 1982. Mass production of microorganisms for biological control. Pages 139–56 in Charudattan, R. and Walker, H. L. (eds) Biological Control of Weeds with Plant Pathogens. John Wiley & Sons, New York.
9. Coenye, T., Laevens, S., Gillis, M. and Vandamme, P. 2001. Genotypic and chemotaxonomic evidence for the reclassification of *Pseudomonas woodsii* (Smith 1911) Stevens 1925 as *Burkholderia andropogonis* (Smith 1911) Gillis et al. 1995. *Int. J. Syst. Evol. Microbiol.*, 51, 183–185.
10. Coenye, T., B. Holmes, K. Kersters, J. R. W. Govan and P. Vandamme. 1999. *Burkholderia cocovenenans* (van Damme et al. 1960) Gillis et al. 1995 and *Burkholderia vandii* Urakami et al. 1994 are junior synonyms of *Burkholderia gladioli* (Severini 1913) Yabuuchi et al.1993 and *Burkholderia plantarii* (Azegami et al. 1987) Urakami et al. 1994, respectively. Int. J. Syst. Bacteriol. 49: 37–42.
11. Coenye, T., S. Laevens, M. Gillis and P Vandamme. 2001a. Genotypic and chemotaxonomic evidence for the reclassification of *Pseudomonas woodsii* (Smith 1911) Stevens 1925 as *Burkholderia andropogonis* (Smith 1911) Gillis et al. 1995. Int. J. Syst. Evol. Microbiol. 51: 183–185.
12. Coenye, T., S. Laevens, A. Willems, M. Ohln, W. Hannant, J. R. W. Govan, M. Gillis, E. Falsen and P. Vandamme. 2001b. *Burkholderia fungorum* sp. nov. and *Burkholderia calcdonica* sp. nov., two new species isolated from the environment, animals and human clinical samples. Int. J. Syst. Evol. Microbiol. 51: 1099–1107.
13. Coenye, T., E. Mahenthiralingam, D. Henry, J. J. LiPuma, S. Laevens, M. Gillis, D. P. Speert and P. Vandamme. 2001c. *Burkholderia ambifaria* sp. nov., a novel member of the *Burkholderia cepacia* complex including biocontrol and cystic fibrosis-related isolates. Int. J. Syst. Evol Microbiol. 51: 1481–1490.
14. Cronquist, A. 1981. An Integrated System of Classification of Flowering Plants. Columbia University Press, New York. Pp. 231–276.
15. Devine, M. D., Marles, M. A. S. and Hall, L. M. 1991. Inhibition of acetolactate synthase is susceptible and resistant biotypes of *Stellaria media*. Pestic. Sci. 31: 273–280.
16. Duke, S. O., F. E. Dayan, A. M. Rimando, K. K. Schrader, G. Aliotta, A. Oliva, and J. G. Romagni. 2002. Chemicals from nature for weed management. Weed Science 50:138–151.
17. Gillis, M., Van, T. V., Bardin, R., Goor, M., Hebbar, P., Willems, A., Segers, P., Kersters, K., Heulin, T., and Fernandez, M. P. 1995. Polyphasic taxonomy in the genus *Burkholderia* leading to an emended description of the genus and proposition of *Burkholderia vietnamiensis* sp. nov. for N2-fixing isolates from rice in Vietnam. *Int. J. Syst. Bacteriol.*, 45, 274–289.
18. Gomez, K. A. and Gomez, A. A. 1984. Statistical Procedures for Agricultural Research. 2nd Edition. John Wiley & Sons, Inc. New York.
19. Goto, M. and M. P. Starr. 1971. A comparative study of *Pseudomonas andropogonis*, *P. stizolobii* and *P. alboprecipitans*. Annals of the phytopathological Society of Japan 37:233–241.
20. Hall, L. M. and Devine, M. D. 1990. Cross-resistance of a chlorsulfuron-resistant biotype of *Stellaria media* to a Triazolopyrimidine herbicide. *Plant Physiol.* 93: 962–966.
21. Hayward, A. C. 1972. A bacterial disease of clover in Hawaii. Plant Disease Reporter 56:446–450.
22. Holm, L. G., Plucknett, D. L., Pancho, J. V. and Herberger, J. P. 1977. The world's worst weeds: distribution and biology. The University Press of Hawaii, Honolulu, Hi.
23. Horsfall, J. G. and R. W. Barrett 1945. An improved grading system for measuring plant diseases. Phytopathol. 35:655.
24. Howard, R. J., J. A. Garland and W. L. Seaman. 1994. Diseases and pests of vegetable crops in Canada: an illustrated compendium. The Canadian Phytopathological Society and Entomological Society of Canada. Ottawa, Ontario. Pp. 554.
25. Hutchinson, J. 1964. The genera of flowering plants (Angiospermae), based principally on the Genera plantarum of G. Bentham and J. D. Hooker/by J. Hutchinson. Oxford at the Clarendon Press. Pp 452–454.
26. Jackson, M. A. 1997. Optimizing nutritional conditions for the liquid culture production of effective fungal biological control agents. J. Ind. Microbiol. Biotech. 19:180–187.
27. Jalas J. and Suominen J. 1987a. Atlas Florae Europaeae: Distribution of vascular plants in Europe III. 6. Caryophyllaceae (Alsinoideae and Paronychioideae). Cambridge University Press, Cambridge Cb2 IRP. Pp. 1–168.
28. Jalas J. and Suominen J. 1987b. Atlas Florae Europaeae: Distribution of vascular plants in Europe III. 6. Caryophyllaceae (Alsinoideae and Paronychioideae) and 7. Caryophyllaceae (Silenoideae). Cambridge University Press, Cambridge Cb2 IRP. Pp. 1–220.
29. Johnson, D. R., Wyse, D. L. and Jones, K. J. 1996. Controlling weeds with phytopathogenic bacteria. Weed Technology 10:621–624.
30. Hu, F.-P., J. M. Young and C. M. Triggs. 1991. Numerical analysis and determinative tests for nonfluorescent plant pathogenic *Pseudomonas* spp. and genomic analysis and reclassification of species related to *Pseudomonas avanae*. Int. J. Syst. Bacteriol. 41: 516–525.
31. Lane, D. J. 1991. 16S/23S rRNA sequencing. In E. Stackebrandt, Goodfellow, M. (ed.) Nucleic Acid Techniques in Bacterial Systematics, pp 115–175. John Wiley and Sons, New York.
32. Liu, D. L.-Y. and Christians, N. E. 1994. Isolation and identification of root-inhibiting compounds from corn gluten hydrolysate. Journal of Plant Growth Regulation 13:227–230.
33. Lutman and Heath, 1990. Variations in the resistance of *Stellaria media* to mecoprop due to biotype, application method and 1-aminobenzotriazole. Weed Res. 30:129–137.
34. Mann, H. H. and Bamers, T. W. 1950. The competition between barley and certain weeds under controlled conditions. 4. Competition with *Stellaria media*. Ann. Appl. Biol. 37:139–148.
35. Martens, J. W., W. L. Seaman, and T. G. Atkinson. 1994. Diseases of Field Crops in Canada: an Illustrated Compendium. The Canadian Phytopathological Society. Ottawa, Ontario. Pp. 160.
36. Mitchell, R. E. and E. J. Frey. 1988. Rhizobitoxine and hydroxythreonine production by *Pseudomonas andropogonis* strains, and the implications to plant disease. Physiol. and Mol. Plant Pathol. 32:335–341.

37. Moffett, M. L., A. C. Hayward and P. C. Fahy. 1986. Five new hosts of *Pseudomonas andropogonis* occurring in eastern Australia: host range and characterization of isolates. Plant Pathology 35:34–43.
38. Moss, E. H. 1983. Flora of Alberta: A manual of flowering plants, Conifers, Ferns and Fern Allies found growing without Cultivation in the Province of Alberta, Canada. Pp 253–260.
39. Nishiyama, K., T. Kusaba, K. Ohta, K. Nahata and K. Ezuka. 1979. Bacterial black rot of tulip caused by *Pseudomonas andropogonis*. Annals of the Phytopathological Society of Japan 45:668–674.
40. O'Donovan, J. T., Jeffers, G. M., Maurice, D., and Sharma, M. P. 1994. Investigation of a chlorsulfuron-resistant chickweed weed [*Stellaria media* (L.) Vill.] population. Can. J. Plant Sci. 74: 693–697.
41. Paisley, R. 1996. MIS whole cell fatty acid analysis by gas chromatography: training manual. MIDI, Newark, Del.
42. Palleroni, N. J. 1984. Genus I. *Pseudomonas* Migula 1894. In Bergey's Mannual of Systematic Bacteriology, vol. 1., pp. 141–199. Edited by N. R. Krieg & J. G. Holt. Baltimore: Williams and Wilkins.
43. SAS Institute Inc. 1987. SAS/STAT Guide for personal computers. Version 6. SAS Institute Inc., Cary, N.C.
44. Scoggan, H. J. 1978. Caryophyllaceae in The Flora of Canada Part 3-Dicotyledoneae (Saururaceae to Violaceae). National Museums of Canada, Ottawa. Pp. 673–710.
45. Stead, D. E. 1992. Grouping of plant-pathogenic and some other *Pseudomonas* spp. by using cellular fatty acid profiles. Int. J. Syst. Bacteriol. 42: 281–295.
46. Stowell, L. J., Nette, K., Heath, B. and Shutter, R. 1989. Fermentation alternatives for commercial production of a mycoherbicide. Pages 219–227 in Demain, A. L., Sornkuti, G. A., Hunter-Cevera, J. C. and Rossmoore, H. W. (eds) Novel Microbial Products for Medicine and Agriculture. Society for Industrial Microbiology.
47. Templeton, G. E. 1982. Biological herbicides: discovery, development, deployment. Weed Sci.:30:430–433.
48. Thomas, A. G., Frick, B. L., and Hall, L., 1997. Weed population shifts in Alberta. Proceedings, 1997 ECW Meetings, Charlottetown, PEI.
49. Thomas, A. G., Frick, B. L., Juras, L. T, Hall, L., van Acker, R., and Loose, D. 1998. Changes in weed distributions indicated by quantitative surveys in the prairie provinces of Canada over 10 years. Proceedings of the 3e Annual WSSA Conference, Chicago, Ill.
50. Toms, H. N. 1964. Plant diseases of Southern British Columbia—A host index. Can. Plant Dis. Surv. 44:143–225. Res. Br., Can. Dep. Agric., Ottawa, Ont.
51. Turkington, R., Kenkel, N. C., and Krankko, G. D. 1980. The biology of Canadian weeds. 42. *Stellaria media* (L.) Vill. Can. J Plant Sci. 60:981–992.
52. Ullstrup, A. J. 1960. Bacterial strip of corn. Phytopathology 50:906–910.
53. Vandamme, P., M. Vancanneyt, B. Pot, L. Mels, B. Hoste, D. Detwettinck, L. Vlaes, C. van den Bone, R. Higgins, J. Hommez, K. Kersters, J.-P. Butzler and H. Goossens. 1992. Polyphasic taxonomic study of the emended genus *Arcobacter* with *Arcobacter butzleri* comb. nov. and *Arcobacter skirrowii* sp. nov., an aerotolerant bacterium isolated from veterinary specimens. Int. J. Syst. Bacteriol. 42: 344–356.
54. Vandamme, P., B. Holnes, M. Vancanneyt, T. Coenye, B. Hoste, R. Coopman, H. Revets, S. Lauwers, M. Gillis, K. Kertsers and J. R. W. Govan. 1997. Occurrence of multiple genomovars of *Burkholderia* cepacia in cyctic fibrosis patients and proposal of *Burkholderia multivorans* sp. nov. Int. J. Syst. Bacteriol. 47: 1188–1200.
55. Vandamme, P., E. Mahenthiralingam, B. Holmes, T. Coenye, B. Hoste, P. de Vos, D. Henry and D. P. Speert. 2000. Identification and population structure of *Burkholderia stabilis* sp. nov. (formerly *Burkholderia cepacia* Genomovar IV). J. Clin. Microbiol. 38: 1042–1047.
56. Viallard, V., I. Poirier, B. Cournoyer, J. Haurat, S. Wiebkin, K. Ophel-Keller and J. Balandreau. 1998. *Burkholderia graminis* sp. nov., a rhizospheric *Burkholderia* species, and reassessment of *[Pseudomonas] phenazinium, [Pseudomonas] pyrrocinia* and *[Pseudomonas] glathei* as *Burkholderia*. Int. J. Syst. Bacteriol. 48: 549–563.
57. Wapshere, A. J. 1974. A strategy for evaluating the safety of organisms for biological weed control. Ann. Appl. Biol. 77:201–211.
58. Watson, A. K. 1985. Host specificity of plant pathogens in biological weed control. In Proceedings of the 6$^{th}$ International Symposium on Biological Control of Weeds, Aug. 19–25, 1984, Vancouver, B.C. Edited by E. S. Delfosse. Agriculture Canada, Ottawa, Ont. Pp. 577–586.
59. Watson, A. K. and L. A. Wymore. 1990. Identifying limiting factors in the biocontrol of weeds. Pages 305–316 in New Directions in the Biological Control: Alternatives for Suppressing Agricultural Pest and Disease. Alan R. Liss, Inc.
60. Watson, A. K. 1993. Biological Control of Weeds Handbook. Weed Science Society of American, Champaign, Ill., USA.
61. Whitford, M. F.; R. J. Forster, C. E. Beard, J. Gong and R. M. Teather. 1998. Phylogenetic analysis of rumen bacteria by comparative sequence analysis of cloned 16S rRNA genes. Anaerobe 4: 153–163.
62. Whitford, M. F.; M. A. McPherson, R. J. Forster and R. M. Teather. 2001. Identification of bacteriocin-like inhibitors from rumen *Streptococcus* spp. and isolation and characterization of Bovicin 255. Appl. Environ. Microbiol. 67: 569–574.
63. Zhang, H., S. Hanada, T. Shigematsu, K. Shibuya, Y. Kamagata, T. Kanagawa and R. Kurane. 2000. *Burkholderia kuruiensis* sp. nov., a trichloroethylene (TCE)-degrading bacterium isolated from an aquifer polluted with TCE. Int. J. Syst. Evol. Microbiol. 50: 743–749.
64. Zidack, N. K., Backman, P. A., and Shaw, J. J. 1992. Promotion of bacterial infection of leaves by an organo-silicone surfactant: implications for biological weed control. Biological Control 2:111–117.

The embodiments of the invention in which an exclusive privilege or property is claimed are defined as follows:

1. A method for suppressing weed growth, comprising applying a composition comprising *Burkholderia andropogonis* (Smith 1911) Gillis et al. 1995, comb. nov., deposited under ATCC Accession No. PTA-4234 and a suitable medium, to a weed belonging to the order Caryophyllales.

2. The method of claim 1, wherein the weed is a member of the family Caryophyllaceae.

3. The method of claim 1, wherein the weed is a member of the subfamily Alsinoideae.

4. The method of claim 1, wherein the weed is a member of the genus Stellaria.

5. A method of suppressing weeds during crop growth comprising:

a) adding an effective amount of a biocontrol composition comprising *Burkholderia andropogonis* (Smith 1911) Gillis et al. 1995, comb. nov., deposited under ATCC Accession No. PTA-4234 and a suitable medium, to an area of plants, and b) growing said plants.

6. A biocontrol composition comprising isolated *Burkholderia andropogonis* (Smith 1911) Gillis et al. 1995, comb. nov., deposited under ATCC Accession No. PTA-4234, and a suitable medium.

7. An isolated bacterial strain having the ATCC designation PTA-4234.

8. A method for suppressing weed growth, comprising applying *Burkholderia andropogonis* (Smith 1911) Gillis et al. 1995, comb. nov., deposited under ATCC Accession No. PTA-4234 to a weed belonging to the order Caryophyllales.

9. The method of claim 8, wherein the weed is a member of the family Caryophyllaceae.

10. The method of claim 8, wherein the weed is a member of the subfamily Alsinoideae.

11. The method of claim 8, wherein the weed is a member of the genus *Stellaria*.

12. The method of claim 1, wherein the composition further comprises a surfactant.

13. The method of claim 5, wherein the composition further comprises a surfactant.

14. The biocontrol composition of claim 6, wherein the composition further comprises a surfactant.

15. The method of claim 12, wherein said surfactant is an organosilicone-based surfactant.

16. The method of claim 13, wherein said surfactant is an organosilicone-based surfactant.

17. The biocontrol composition of claim 14, wherein said surfactant is an organosilicone-based surfactant.

* * * * *

SEQUENCE LISTING

<160> NUMBER OF SEQ ID NOS: 6

<210> SEQ ID NO 1
<211> LENGTH: 17
<212> TYPE: DNA
<213> ORGANISM: Artificial Sequence
<220> FEATURE:
<223> OTHER INFORMATION: Primer FP1 used to amplify 16S ribosomal rRNA
      genes

<400> SEQUENCE: 1
agagttygat yctggct                                                  17

<210> SEQ ID NO 2
<211> LENGTH: 21
<212> TYPE: DNA
<213> ORGANISM: Artificial Sequence
<220> FEATURE:
<223> OTHER INFORMATION: Primer R1492 used to amplify 16S ribosomal rRNA
      genes

<400> SEQUENCE: 2
tacggytacc ttgttacgac t                                             21

<210> SEQ ID NO 3
<211> LENGTH: 17
<212> TYPE: DNA
<213> ORGANISM: Artificial Sequence
<220> FEATURE:
<223> OTHER INFORMATION: IRD800-labeled 16S rDNA specific primers FP1

<400> SEQUENCE: 3
actcctacgg caggcag                                                  17

<210> SEQ ID NO 4
<211> LENGTH: 18
<212> TYPE: DNA
<213> ORGANISM: Artificial Sequence
<220> FEATURE:
<223> OTHER INFORMATION: IRD800-labeled 16S rDNA specific primers FP1

<400> SEQUENCE: 4
gwattaccgc ggckgctg                                                 18

<210> SEQ ID NO 5
<211> LENGTH: 20
<212> TYPE: DNA
<213> ORGANISM: Artificial Sequence
<220> FEATURE:
<223> OTHER INFORMATION: IRD800-labeled 16S rDNA specific primers FP1

<400> SEQUENCE: 5
aaactyaaak gaattgacgg                                               20

<210> SEQ ID NO 6
<211> LENGTH: 16
<212> TYPE: DNA
<213> ORGANISM: Artificial Sequence
<220> FEATURE:
<223> OTHER INFORMATION: IRD800-labeled 16S rDNA specific primers FP1

<400> SEQUENCE: 6
agggttgcgc tcgttg                                                   16